US 11,779,412 B2

(12) United States Patent
Ida et al.

(10) Patent No.: US 11,779,412 B2
(45) Date of Patent: Oct. 10, 2023

(54) ROBOTICALLY-ASSISTED SURGICAL DEVICE, ROBOTICALLY-ASSISTED SURGERY METHOD, AND SYSTEM

(71) Applicants: Medicaroid Corporation, Kobe (JP); Ziosoft, Inc., Tokyo (JP)

(72) Inventors: Jota Ida, Kobe (JP); Yukihiko Kitano, Kobe (JP); Shusuke Chino, Tokyo (JP); Tsuyoshi Nagata, Tokyo (JP); Yutaka Karasawa, Tokyo (JP); Shinichiro Seo, Tokyo (JP)

(73) Assignees: MEDICAROID CORPORATION, Kobe (JP); ZIOSOFT, INC., Tokyo (JP)

( * ) Notice: Subject to any disclaimer, the term of this patent is extended or adjusted under 35 U.S.C. 154(b) by 503 days.

(21) Appl. No.: 16/599,310

(22) Filed: Oct. 11, 2019

(65) Prior Publication Data
US 2020/0113635 A1 Apr. 16, 2020

(30) Foreign Application Priority Data
Oct. 11, 2018 (JP) ................................ 2018-192930

(51) Int. Cl.
*A61B 34/30* (2016.01)
*A61B 90/00* (2016.01)
(Continued)

(52) U.S. Cl.
CPC .............. *A61B 34/30* (2016.02); *A61B 90/37* (2016.02); *A61B 90/50* (2016.02);
(Continued)

(58) Field of Classification Search
CPC combination set(s) only.
See application file for complete search history.

(56) References Cited

U.S. PATENT DOCUMENTS 7,623,679 B2 11/2009 West et al.
8,086,008 B2 12/2011 Coste-Maniere et al.
(Continued)

FOREIGN PATENT DOCUMENTS

JP   2011-131020 A   7/2011
JP       5408493 A   2/2014
(Continued)

OTHER PUBLICATIONS

Bano et al. ("Simulation of Pneumoperitoneum for Laparoscopic Surgery Planning", Oct. 2012) (Year: 2012).*
(Continued)

*Primary Examiner* — Scott Luan
(74) *Attorney, Agent, or Firm* — Rankin, Hill & Clark LLP

(57) ABSTRACT

A robotically-assisted surgical device assists robotic surgery with a surgical robot including a robot arm, and includes a processing unit and a display unit. The processing unit acquires 3D data of a subject; acquires kinematic information of the robot arm; acquires information of a surgical procedure for operating; acquires position planning information for a plurality of ports to be pierced on a body surface of the subject; acquires measurement information obtained by measuring a position of a first port pierced on the body surface among the plurality of ports; determines a position of at least one of remaining ports other than the first port, based on the measurement information of the position of the first port, the information of the surgical procedure, the kinematic information, and the 3D data; and causes the display unit to display information indicating the determined position of the remaining port.

20 Claims, 16 Drawing Sheets

(51) Int. Cl.
*A61B 90/50* (2016.01)
*A61B 34/20* (2016.01)
*A61B 17/34* (2006.01)
*A61B 34/00* (2016.01)
*A61B 34/10* (2016.01)

(52) U.S. Cl.
CPC ..... *A61B 17/3423* (2013.01); *A61B 2034/105* (2016.02); *A61B 2034/107* (2016.02); *A61B 2034/2048* (2016.02); *A61B 2034/252* (2016.02); *A61B 2034/302* (2016.02); *A61B 2090/366* (2016.02); *A61B 2090/367* (2016.02)

(56) References Cited

U.S. PATENT DOCUMENTS

| | | | |
|---|---|---|---|
| 3,311,300 | A1 | 11/2012 | Matsumoto |
| 2003/0109780 | A1 | 6/2003 | Coste-Maniere et al. |
| 2006/0167440 | A1 | 7/2006 | Cooper et al. |
| 2007/0156122 | A1 | 7/2007 | Cooper |
| 2007/0167784 | A1 | 7/2007 | Shekhar et al. |
| 2007/0249911 | A1* | 10/2007 | Simon ............... G16H 70/20 600/300 |
| 2009/0163931 | A1 | 6/2009 | Cooper et al. |
| 2011/0023285 | A1 | 2/2011 | Cooper |
| 2011/0023651 | A1 | 2/2011 | Cooper |
| 2012/0253515 | A1 | 10/2012 | Coste-Maniere et al. |
| 2012/0277764 | A1 | 11/2012 | Cooper et al. |
| 2013/0060278 | A1 | 3/2013 | Bozung et al. |
| 2013/0096576 | A1 | 4/2013 | Cooper et al. |
| 2014/0100620 | A1 | 4/2014 | Mullaney |
| 2014/0148816 | A1 | 5/2014 | McDonald et al. |
| 2014/0243852 | A1 | 8/2014 | Cooper et al. |
| 2014/0316412 | A1 | 10/2014 | Janik et al. |
| 2015/0182295 | A1 | 7/2015 | Bozung et al. |
| 2016/0157946 | A1 | 6/2016 | Cooper |
| 2017/0156799 | A1 | 6/2017 | Bozung |
| 2017/0245947 | A1 | 8/2017 | Bozung et al. |
| 2018/0200008 | A1 | 7/2018 | Cooper |
| 2018/0214241 | A1* | 8/2018 | Furuta ............... A61B 34/20 |
| 2018/0256270 | A1 | 9/2018 | Cooper et al. |
| 2019/0321115 | A1 | 10/2019 | Anderson et al. |
| 2021/0106394 | A1 | 4/2021 | Cooper et al. |
| 2021/0307851 | A1 | 10/2021 | Anderson et al. |
| 2021/0378751 | A1 | 12/2021 | Bozung |

FOREIGN PATENT DOCUMENTS

| | | |
|---|---|---|
| JP | 2015-502180 A | 1/2015 |
| JP | 2018-196780 A | 12/2018 |
| JP | 2021-528114 A | 10/2021 |
| WO | 2019/203860 A1 | 10/2019 |

OTHER PUBLICATIONS

From, Pål Johan, "On the Kinematics of Robotic-assisted Minimally Invasive Surgery", Modeling Identication and Control, vol. 34, No. 2, 2013, pp. 69-82.

Hayashibe, Mitsuhiro, et al., "Robotic surgery setup simulation with the integration of inverse-kinematics computation and medical imaging", Computer Methods and Programs in Biomedicine, vol. 83 (2006), pp. 63-72.

Kitasaka, Takayuki, et al., "Virtual Pneumoperitoneum for Generating Virtual Laparoscopic Views Based on Volumetric Deformation", MIC-CAI (Medical Image Computing and Computer-Assisted Intervention), 2004, pp. 559-567.

Selha, Shaun, et al., "Dexterity Optimization by Port Placement in Robot-Assisted Minimally Invasive Surgery", SPIE International Symposium on Intelligent Systems and Advanced Manufacturing, Newton, MA Oct. 28-31, 2001.

Zhi, Li, et al., "Design of a Multi-Arm Surgical Robotic System for Dexterous Manipulation", Journal of Mechanisms and Robotics, 2016.

Japanese Office Action dated May 10, 2022, Application No. JP 2018-192930, English translation included, (8 pages).

Japanese Office Action dated May 10, 2022, issued in the corresponding Japanese Application No. 2018-192931 of related U.S. Appl. No. 16/599,414; English translation included, 5 pages.

* cited by examiner

ROBOTICALLY-ASSISTED SURGICAL DEVICE, ROBOTICALLY-ASSISTED SURGERY METHOD, AND SYSTEM

CROSS-REFERENCE TO RELATED APPLICATIONS

This application is based on and claims priority under 35 USC 119 from Japanese Patent Application No. 2018-192930 filed on Oct. 11, 2018, the contents of which are incorporated herein by reference.

TECHNICAL FIELD

The present disclosure relates to a robotically-assisted surgical device that assists robotic surgery with a surgical robot, a robotically-assisted surgery method, and a system.

BACKGROUND ART

In the related art, when minimally invasive robotic surgery is operated using a surgical robot, a port is pierced to insert forceps into a body of a patient being operated. The position of the port is approximately determined depending on a surgical procedure, but the optimal position thereof has yet to be established. US2014/0148816A discloses port placement planning. Specifically, a surgical port placement system disclosed in US2014/0148816A generates a surgical port placement model based on a plurality of parameter sets associated with a plurality of past surgical procedures, receives a given parameter set for a given surgical procedure including physical characteristics of a given patient, and plans at least one port position for the given patient for the given surgical procedure based on the given parameter set and the surgical port placement model.

SUMMARY OF INVENTION

The present disclosure provides a robotically-assisted surgical device capable of reducing the influence of misplacement of a pre-pierced port (a port that has been previously pierced) on robotic surgery, a robotically-assisted surgery method, and a system.

According to one aspect of the disclosure, a robotically-assisted surgical device assists minimally invasive robotic surgery with a surgical robot that includes at least one robot arm holding a surgical instrument. The robotically-assisted surgical device includes a processing unit and a display unit. The processing unit is configured to: acquire 3D data of a subject; acquire kinematic information regard to the robot arm; acquire information of a surgical procedure for operating the subject; acquire position planning information for a plurality of ports which are to be pierced on a body surface of the subject; acquire measurement information obtained by measuring a position of a first port which is pierced on the body surface among the plurality of ports; determine a position of at least one of remaining ports other than the first port among the plurality of ports, based on the measurement information of the position of the first port, the information of the surgical procedure, the kinematic information, and the 3D data; and cause the display unit to display information indicating the determined position of the at least one of remaining ports.

According to another aspect of the disclosure, a robotically-assisted surgery method is a method of a robotically-assisted surgical device that assists robotic surgery with a surgical robot that includes at least one robot arm holding a surgical instrument. The robotically-assisted surgery method includes: acquiring 3D data of a subject; acquiring kinematic information regard to a moving part of the surgical robot for performing the robotic surgery; acquiring information of a surgical procedure for operating the subject; acquiring position planning information for a plurality of ports which are to be pierced on a body surface of the subject; acquiring measurement information obtained by measuring a position of a first port which is pierced on the body surface among the plurality of ports; determining a position of at least one of remaining ports other than the first port among the plurality of ports, based on the measurement information of the position of the first port, the information of the surgical procedure, the kinematic information, and the 3D data; and causing a display unit to display information indicating the determined position of the at least one of remaining ports.

According to further another aspect of the disclosure, a robotically-assisted surgery system is a system of a robotically-assisted surgical device that assists robotic surgery with a surgical robot that includes at least one robot arm holding a surgical instrument. The robotically-assisted surgery system includes, acquiring 3D data of a subject; acquiring kinematic information regard to a moving part of the surgical robot for performing the robotic surgery; acquiring information of a surgical procedure for operating the subject; acquiring position planning information for a plurality of ports which are to be pierced on a body surface of the subject; acquiring measurement information obtained by measuring a position of a first port which is pierced on the body surface among the plurality of ports; determining a position of at least one of remaining ports other than the first port among the plurality of ports, based on the measurement information of the position of the first port, the information of the surgical procedure, the kinematic information, and the 3D data; and causing a display unit to display information indicating the determined position of the at least one of remaining ports.

According to the present disclosure, the present disclosure can suppress deterioration in workability of robotic surgery by a surgical robot

DESCRIPTION OF EMBODIMENTS

Hereinafter, embodiments of the present disclosure will be described using the drawings.

In the present disclosure, a robotically-assisted surgical device assists minimally invasive robotic surgery with a surgical robot that includes at least one robot arm holding a surgical instrument. The robotically-assisted surgical device includes a processing unit and a display unit. The processing unit is configured to: acquire 3D data of a subject; acquire kinematic information regard to the robot arm; acquire information of a surgical procedure for operating the subject; acquire position planning information for a plurality of ports which are to be pierced on a body surface of the subject; acquire measurement information obtained by measuring a position of a first port which has been pierced on the body surface among the plurality of ports; determine a position of at least one of remaining ports other than the first port among the plurality of ports, based on the acquired measurement information of the position of the first port, the acquired information of the surgical procedure, the acquired kinematic information, and the acquired 3D data; and cause the display unit to display information indicating the determined position of the at least one of remaining ports.

According to the present disclosure, even when one port is pierced at a position misplaced from the piercing-planned position, the robotically-assisted surgical device can adjust the remaining port positions in consideration of the port position of the pre-pierced port. Accordingly, even when the operation efficiency or the safety of robotic surgery is likely to deteriorate with the derived combination of the plurality of port positions due to the error of the piercing position of the pre-pierced port, deterioration in the operation efficiency and the safety can be suppressed by replacing the remaining port positions in consideration of the pre-pierced port.

Circumstances for Achievement of Aspect of Present Disclosure

Figure 14:
FIG. 14 is a view illustrating designation of a piercing position on a 2D plane and misplacement of the piercing position in a 3D space.

In some cases, an assistant pierces a port according to preoperative planning. However, it is difficult to accurately pierce a port at a planned port position. When a port position to be pierced is preoperatively planned on a 2D plane, for example, a port is planned to be pierced at a position at a distance L1 from a navel, as illustrated in FIG. 14, even with the same distance on the 2D plane, the position largely changes in a forward-backward direction of a subject as it moves toward a lateral part of the subject (refer to a range α). Therefore, it is difficult to accurately perform the measurement and to uniquely determine a port position to be pierced during port piercing.

In addition, in robotic surgery, pneumoperitoneum is performed in many cases. During pneumoperitoneum, carbon dioxide gas is injected into an abdominal cavity to secure a working space in the abdominal cavity. Since the degree of elevation of abdominal wall varies depending on the pneumoperitoneum state, a 3D position planned on a body surface of a patient is also variable.

Therefore, a port may be pierced at a position misplaced from a planned port position. In port position planning, a combination of a plurality of ports is planned. However, when one port position among the plurality of port positions is misplaced, during robotic surgery using a port set including this port position, the workability of a surgical robot may deteriorate. For example, when a pierced port position (pre-pierced port) is misplaced from a planned port position, there may be a region that cannot be reached by forceps in a body of a patient, or robot arms with forceps that are included in a surgical robot may come into contact with each other such that a movable range of the robot arms is limited. In addition, during minimally invasive surgery using a surgical robot, application of stress to a port is limited as compared to the minimally invasive surgery by persons.

In the following embodiment, a robotically-assisted surgical device capable of reducing the influence of misplacement of a pre-pierced port on robotic surgery, a robotically-assisted surgery method, and a system will be described.

First Embodiment

Figure 1:
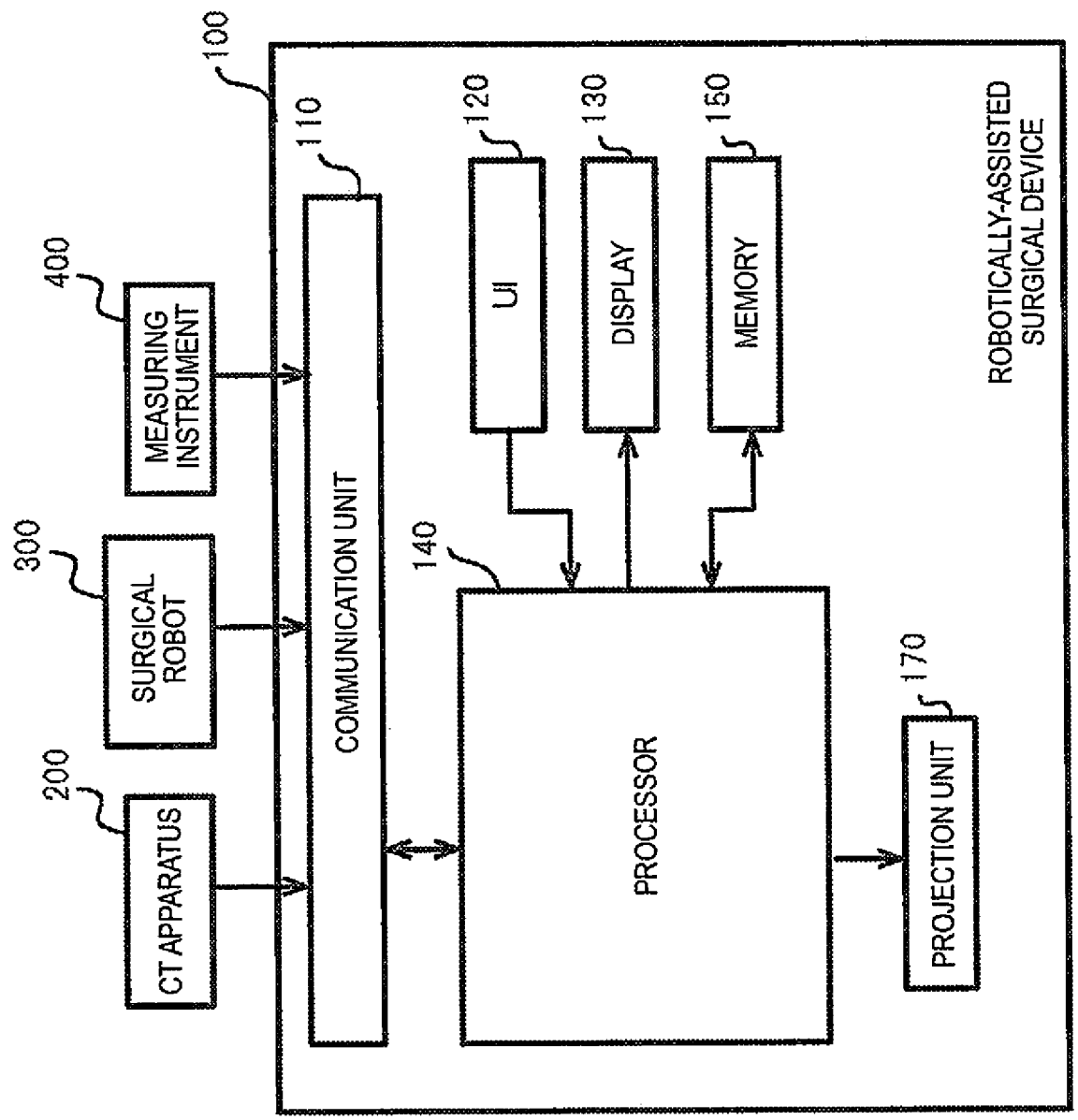
FIG. 1 is a block diagram illustrating a hardware configuration example of a robotically-assisted surgical device according to a first embodiment.

FIG. 1 is a block diagram illustrating a configuration example of a robotically-assisted surgical device 100 according to a first embodiment. The robotically-assisted surgical device 100 assists robotic surgery with a surgical robot 300 and performs, for example, a preoperative simulation, an intraoperative simulation, and intraoperative navigation.

The surgical robot 300 includes a robot operation terminal, a robot main body, and an image display terminal.

The robot operation terminal includes a hand controller or a foot switch manipulated by an operator. The robot operation terminal operates a plurality of robot arms AR provided in the robot main body according to a manipulation of the hand controller or the footswitch by the operator. In addition, the robot operation terminal includes a viewer. The viewer may be a stereo viewer and may merge images input through an endoscope to display a 3D image. A plurality of robot operation terminals may be present such that a plurality of operators operate the plurality of robot operation terminals to perform robotic surgery.

The robot main body includes: a plurality of robot arms for performing robotic surgery; and an end effector EF (forceps, an instrument) as a surgical instrument that is mounted on the robot arm AR.

The robot main body of the surgical robot 300 includes four robot arms AR including: a camera arm on which an endoscope camera is mounted; a first end effector arm on which an end effector EF operated by a right-hand controller of the robot operation terminal is mounted; a second end effector arm on which an end effector EF operated by a left-hand controller of the robot operation terminal is mounted; and a third end effector arm on which an end effector EF for replacement is mounted. Each robot arm AR includes a plurality of joints and includes a motor and an encoder corresponding to each joint. Each robot arm AR has at least 6 degrees of freedom and preferably 7 or 8 degrees of freedom, operates in a 3D space, and may be movable in each direction in the 3D space. The end effector EF is an instalment that actually comes into contact with a treatment target in a subject PS during robotic surgery, and can perform various treatments (for example, gripping, dissection, exfoliation, or suture).

Examples of the end effector EF may include gripping forceps, exfoliating forceps, an electric knife, and the like. A plurality of different end effectors EF may be prepared for respective functions. For example, in robotic surgery, a treatment of dissecting a tissue with one end effector EF while holding or pulling the tissue with two end effectors EF may be performed. The robot arm AR and the end effector EF may operate based on an instruction from the robot operation terminal.

The image display terminal includes a monitor, a controller for processing an image captured by a camera of an endoscope to display the image on a viewer or a monitor, and the like. The monitor is checked by, for example, an assistant of robotic surgery or a nurse.

The surgical robot 300 receives a manipulation of the hand controller or the footswitch of the robot operation terminal by the operator, controls the operation of the robot arm AR or the end effector EF of the robot main body, and performs robotic surgery in which various treatments are performed on the subject PS. In robotic surgery, laparoscopic surgery is performed in the subject PS.

In robotic surgery, a port PT is pierced on the body surface of the subject PS, and pneumoperitoneum is performed through the port PT. In pneumoperitoneum, carbon dioxide may be injected to inflate the abdominal cavity of the subject PS. In the port PT, a trocar TC may be provided. The trocar TC includes a valve and maintains the inside of the subject PS to be airtight. In addition, in order to maintain the airtight state, air (for example, carbon dioxide) is intermittently introduced into the subject PS.

The end effector EF (shaft of the end effector EF) is inserted into the trocar TC. The valve of the trocar TC is opened during insertion of the end effector EF and is closed during the separation of the end effector EF. The end effector EF is inserted from the port PT through the trocar TC such that various treatments are performed according to the surgical procedure. Robotic surgery may be applied to not only laparoscopic surgery in which the surgery target is the abdomen but also arthroscopic surgery in which the surgery target includes a region other than the abdomen.

As illustrated in FIG. 1, the robotically-assisted surgical device 100 includes a communication unit 110, a user interface (UI) 120, a display 130, a processor 140, and a memory 150. The UI 120, the display 130, and the memory 150 may be included in the robotically-assisted surgical device 100 or may be provided separately from the robotically-assisted surgical device 100.

A CT (Computed Tomography) apparatus 200 is connected to the robotically-assisted surgical device 100 through the communication unit 110. The robotically-assisted surgical device 100 acquires volume data from the CT apparatus 200 and processes the acquired volume data. The robotically-assisted surgical device 100 may be configured by a PC (Personal Computer) and software installed on the PC. The robotically-assisted surgical device 100 may be configured as a part of the surgical robot 300.

The surgical robot 300 is connected to the robotically-assisted surgical device 100 through the communication unit 110. The robotically-assisted surgical device 100 may provide various data, information, or images from, for example, the surgical robot 300 to assist robotic surgery. The robotically-assisted surgical device 100 may acquire, from, for example, the surgical robot 300, information regarding a mechanism or the operation of the surgical robot 300 or data obtained before, during, or after robotic surgery such that various kinds of analysis or interpretation can be performed based on the acquired information or data. The analysis result or the interpretation result may be visualized.

A measuring instrument 400 is connected to the robotically-assisted surgical device 100 through the communication unit 110. The measuring instrument 400 may measure information (for example, a body surface position of the subject PS) regarding the subject PS (for example, a patient) to be operated by the surgical robot 300. The measuring instrument 400 may measure a position of the port PT provided on the body surface of the subject PS. The measuring instrument 400 may be, for example, a depth sensor 410. The depth sensor 410 may be included in the surgical robot 300 (for example, the robot main body) or may be provided in the ceiling or the like of an operating room where robotic surgery is performed. In addition, the measuring instrument 400 may receive an input of the result of manual measurement of an operation unit of the measuring instrument 400. In the manual measurement, for example, information regarding a patient or a port position on the body surface may be measured by a ruler or a tape measure.

In addition, the CT apparatus 200 is connected to the robotically-assisted surgical device 100. Alternatively, instead of the CT apparatus 200, a device capable of capturing various images may be connected to the robotically-assisted surgical device 100. This device may be, for example, an angiographic device or an ultrasound device. This device may be used to check the internal state of the subject PS before and during robotic surgery.

The CT apparatus 200 irradiates an organism with X-rays and acquires images (CT images) using a difference in X-ray absorption depending on tissues. The subject PS may be, for example, a human body or an organism. The subject PS may not be a human body nor an organism. For example, the subject PS may be an animal or a phantom for surgical training.

A plurality of CT images may be acquired m a time series. The CT apparatus 200 generates volume data including information regarding any portion inside the organism. Here, any portion inside the organism may include various organs (for example, brain, heart, kidney, colon, intestine, lung, chest, lacteal gland, and prostate gland). By acquiring the CT image, it is possible to obtain a pixel value (CT value, voxel value) of each pixel (voxel) of the CT image. The CT apparatus 200 transmits the volume data as the CT image to the robotically-assisted surgical device 100 via a wired circuit or a wireless circuit.

Specifically, the CT apparatus 200 includes a gantry (not illustrated) and a console (not illustrated). The gantry includes an X-ray generator (not illustrated) and an X-ray detector (not illustrated) and acquires images at a predetermined timing instructed by the console to detect an X-ray transmitted through the subject PS and to obtain X-ray detection data. The X-ray generator includes an X-ray tube (not illustrated). The console is connected to the robotically-assisted surgical device 100. The console acquires a plurality of X-ray detection data from the gantry and generates volume data based on the X-ray detection data. The console transmits the generated volume data to the robotically-assisted surgical device 100. The console may include an operation unit (not illustrated) for inputting patient information, scanning conditions regarding CT scanning, contrast enhancement conditions regarding contrast medium administration, and other information. This operation unit may include an input device such as a keyboard or a mouse.

The CT apparatus 200 continuously captures images to acquire a plurality of 3D volume data such that a moving image can also be generated. Data of the moving image generated the plurality of 3D volume data will also be referred to as 4D (four-dimensional) data.

The CT apparatus 200 may capture CT images at each of a plurality of timings. The CT apparatus 200 may capture a CT image in a state where the subject PS is contrast-enhanced. The CT apparatus 200 may capture a CT image in a state where the subject PS is not contrast-enhanced.

In the robotically-assisted surgical device 100, the communication unit 110 performs communication of various data or information with other devices. The communication unit 110 may perform communication of various data with the CT apparatus 200, the surgical robot 300, and the measuring instrument 400. The communication unit 110 performs wired communication or wireless communication The communication unit 110, may be connected to the CT apparatus 200, the surgical robot 300, and the measuring instrument 400 in a wired or wireless manner.

The communication unit 110 may acquire various information for robotic surgery from the surgical robot 300. The various information may include, for example, kinematic information of the surgical robot 300. The communication unit 110 may transmit various information for robotic surgery to the surgical robot 300. The various information may include, for example, information (for example, an image or data) generated by a processing unit 160.

The communication unit 110 may acquire various information for robotic surgery from the measuring instrument 400. The various information may include, for example, position information of the body surface of the subject PS or information of a port position pierced on the body surface of the subject PS that is measured by the measuring instrument 400.

The communication unit 110 may acquire volume data from the CT apparatus 200. The acquired volume data may be transmitted immediately to the processor 140 for various processes, or may be stored in the memory ISO first and then transmitted to the processor 140 for various processes as necessary. In addition, the volume data may be acquired via a recording medium.

The volume data acquired by the CT apparatus 200 may be transmitted from the CT apparatus 200 to an image data server such as (PACS: Picture Archiving and Communication Systems; not illustrated) and stored therein, instead of acquiring from the CT apparatus 200, the communication unit 110 may acquire volume data from the image data server. This way, the communication unit 110 functions as an acquisition unit that acquires various data such as volume data.

The UI 120 may include a touch panel, a pointing device, a keyboard, or a microphone. The UI 120 receives an input operation from a user of the robotically-assisted surgical device 100. The user may include a doctor, a radiographer, or other paramedic staffs. The doctor may include an operator that manipulates the robot operation terminal to operate robotic surgery or an assistant that assists robotic surgery near the subject PS.

The UI 120 receives an operation such as a designation of a region of interest (ROI), a setting of luminance conditions, and the like in the volume data. The region of interest may include various tissues (such as blood vessels, bronchial tubes, organs, bones, brain, heart, feet, neck, and blood flow). The tissues may broadly include tissues of the subject PS such as diseased tissue, normal tissue, organs, and parts. In addition, the UI 120 may receive an operation such as a designation of the region of interest or a setting of luminance conditions in the volume data with respect to an image (for example, a 3D image or a 2D image described below) based on the volume data.

The display 130 may include a Liquid Crystal Display (LCD) and displays various information. The various information may include a 3D image or a 2D image obtained from the volume data. The 3D image may include, for example, a volume rendering image, a surface rendering image, a virtual endoscope image (VE image), a virtual ultrasound image, or a Curved Planar Reconstruction (CPR) image. The volume rendering image may include a RaySum image (also simply referred to as "SUM image"), a Maximum Intensity Projection (MIP) image, a Minimum Intensity Projection (MinIP) image, an average image, or a Raycast image. The 2D image may include an axial image, a sagittal image, a coronal image, a Multi Planar Reconstruction (MPR) image, or the like. The 3D image and the 2D image may include a color fusion image.

The memory 150 includes a primary storage device such as various Read Only Memories (ROM) or Random Access Memory (RAM). The memory 150 may include a secondary storage device such as a Hard Disk Drive (HDD) or a Solid State Drive (SSD). The memory 150 may include a third storage device such as a USB memory or an SD card. The memory 150 stores various information. The various information includes information acquired via the communication unit 110, information and an image generated from the processor 140, setting information set by the processor 140, and various programs. The information acquired via the communication unit 110 may include, for example, information from the CT apparatus 200 (for example, volume data), information from the surgical robot 300, information from the measuring instrument 400, and information from an external server. The memory 150 is an example of a non-transitory recording medium in which a program is recorded.

A projection unit 170 projects visible light (for example, laser light) to the subject. The projection unit 170 projects the visible light to display various information (for example, the information of the port position) on the body surface of the subject PS (for example, the body surface of the abdomen). The visible light, that is, the information displayed on the body surface of the subject PS is recognized by the users (for example, an assistant).

The processor 140 may include a Central Processing Unit (CPU), a Digital Signal Processor (DSP), or a Graphical Processing Unit (GPU). The processor 140 executes the program stored in the memory 150 to function as the processing unit 160 controlling various processes and controls.

Figure 2:
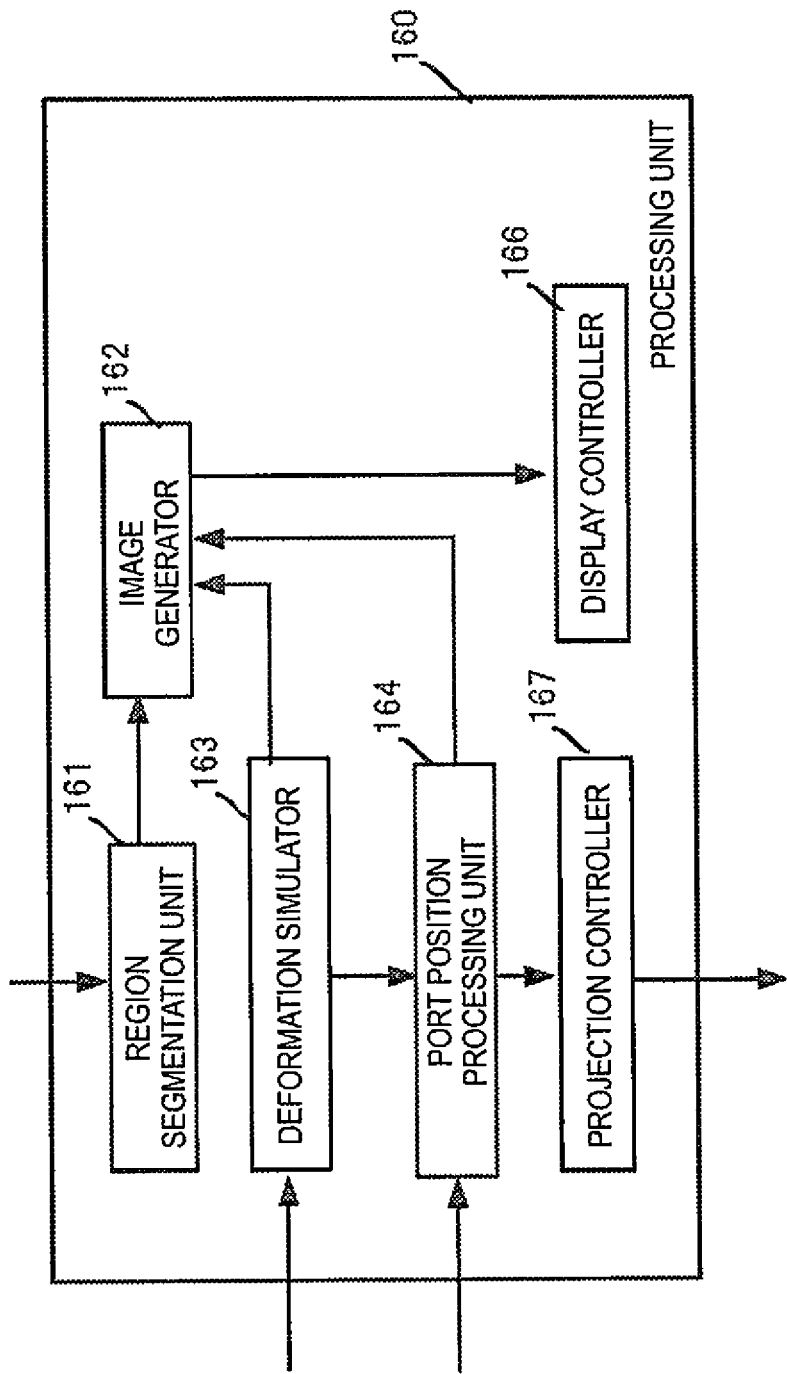
FIG. 2 is a block diagram illustrating a functional configuration example of the robotically-assisted surgical device.

FIG. 2 is a block diagram illustrating a functional configuration example of the processing unit 160.

The processing unit 160 includes a region segmentation unit 161, an image generator 162, a deformation simulator 163, a port position processing unit 164, a display controller 166, and a projection controller 167.

The processing unit 160 integrates the respective units of the robotically-assisted surgical device 100. The respective sections included in the processing unit 160 may be implemented as different functions by one piece of hardware or may be implemented as different functions by a plurality of pieces of hardware. In addition, the respective sections included in the processing unit 160 may be implemented by a dedicated hardware component.

The region segmentation unit 161 may perform segmentation processing in the volume data. In this case, the UI 120 receives an instruction from a user and transmits information of the instruction to the region segmentation unit 161. The region segmentation unit 161 may perform segmentation processing from the volume data based on the information of the instruction using a well-known method to segment the region of interest. In addition, the region of interest may be set manually in accordance with the specific instruction from the user. In addition, when an observation target is predetermined, the region segmentation unit 161 may perform segmentation processing from the volume data to segment the region of interest including the observation target without the user instruction. The segmented region may include regions of various tissues (for example, blood vessels, bronchial tubes, organs, bones, brain, heart, feet, neck, blood flow, lacteal gland, chest, and tumor). The observation target may be a target to be treated by robotic surgery.

The image generator 162 may generate a 3D image or a 2D image based on the volume data acquired from the communication unit 110. The image generator 162 may generate a 3D image or a 2D image from the volume data acquired from the communication unit 110 based on a designated region or the region segmented by the region segmentation unit 161.

The deformation simulator 163 may perform a process relating to deformation in the subject PS as a surgery target. For example, the deformation simulator 163 may perform a pneumoperitoneum simulation of virtually performing pneumoperitoneum on the subject PS. A specific method of the pneumoperitoneum simulation may be a well-known method, for example, a method described in Takayuki Kitasaka, Kensaku Mori, Yuichiro Hayashi, Yasuhito Suenaga, Makoto Hashizume, and Junichiro Toriwaki, "Virtual Pneumoperitoneum for Generating Virtual Laparoscopic Views Based on Volumetric Deformation", MICCAI (Medical Image Computing and Computer-Assisted Intervention), 2004, P559-P567 which is incorporated herein by reference. That is, the deformation simulator 163 may perform the pneumoperitoneum simulation based on the volume data (volume data before pneumoperitoneum (non-pneumoperitoneum state)) acquired from the communication unit 110 or the region segmentation unit 161 to generate volume data after pneumoperitoneum (volume data in the pneumoperitoneum state). Through the pneumoperitoneum simulation, the user can simulate a state where pneumoperitoneum is performed on the subject PS without actually performing pneumoperitoneum on the subject PS to observe a state where pneumoperitoneum is virtually performed. Among pneumoperitoneum states, a state of pneumoperitoneum estimated by the pneumoperitoneum simulation will be referred to as "a virtual pneumoperitoneum state", and a state where pneumoperitoneum is actually performed will also be referred to as "an actual pneumoperitoneum state".

Figure 3:
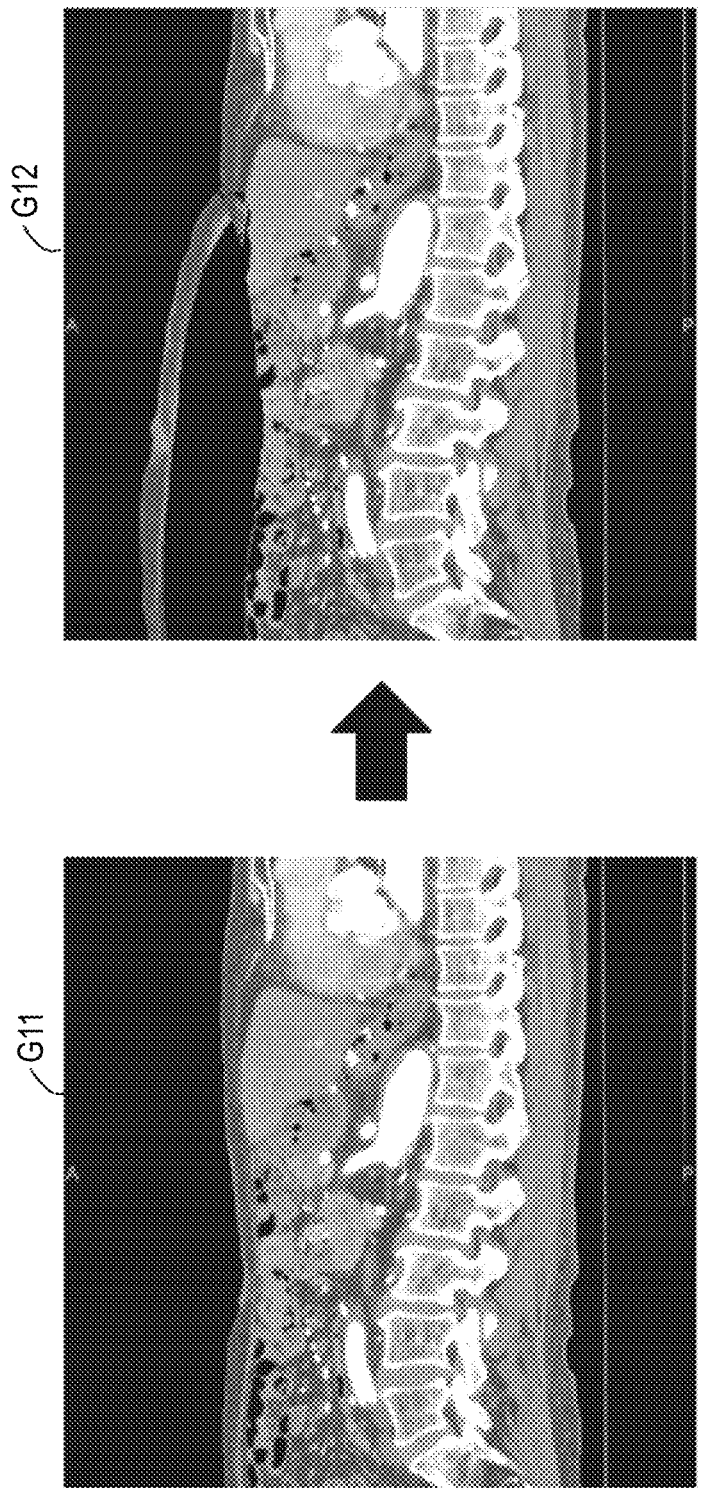
FIG. 3 is a view illustrating examples of MPR images of an abdomen before and after performing a pneumoperitoneum simulation.

FIG. 3 is a view illustrating examples of MPR images of the abdomen before and after performing the pneumoperitoneum simulation. An image G11 illustrate the state before performing the pneumoperitoneum simulation, which is a state (non-pneumoperitoneum state) where the abdomen of the subject PS is not inflated. An image G12 illustrate the state after performing the pneumoperitoneum simulation, which is a state (virtual pneumoperitoneum state) where the abdomen of the subject PS is inflated and includes a pneumoperitoneum space KS. In robotic surgery, the subject PS is operated in the pneumoperitoneum state. Therefore, the pneumoperitoneum simulation is performed on the volume data acquired in the non-pneumoperitoneum state by the deformation simulator 163 and the volume data in the virtual pneumoperitoneum state is derived.

The deformation simulator 163 may virtually deform the observation target such as an organ or a disease in the subject PS. The observation target may be a surgery target to be operated by the operator. The deformation simulator 163 may simulate a state where an organ is pulled, pressed, or dissected by the end effector EF. In addition, the deformation simulator 163 may simulate, for example, movement of an organ by a postural change.

The port position processing unit 164 acquires information of a plurality of ports PT provided on the body surface of the subject PS. The information of the port PT may include, for example, identification information of the port PT, information regarding a position (port position) on the body surface of the subject PS where the port PT is pierced, information regarding the size of the port PT, or the like. The information of a plurality of ports may be stored in the memory 150 or the external server as a template. The information of the plurality of ports may be determined according to the surgical procedure. The information of the plurality of ports may be used for preoperative planning.

The port position processing unit 164 may acquire the information of the plurality of ports positions from the memory 150. The port position processing unit 164 may acquire the information of the plurality of port positions from the external server via the communication unit 110. The port position processing unit 164 may receive a designation of port positions of the plurality of ports PT via the UI 120 to acquire the information of the plurality of port positions. The information of the plurality of ports may be the information of a combination of the plurality of port positions.

The port position processing unit 164 acquires kinematic information of the surgical robot 300. The kinematic information may be stored in the memory 150. The port position processing unit 164 may acquire the kinematic information from the memory 150. The port position processing unit 164 may acquire the kinematic information from the surgical robot 300 or the external server via the communication unit 110. The kinematic information may vary depending on the surgical robot 300.

The kinematic information may include, for example, shape information regarding the shape of an instrument (for example, the robot arm AR or the end effector EF) for robotic surgery included in the surgical robot 300 or operation information regarding the operation thereof. This shape information may include information of at least a part, for example, the length or weight of each portion of the robot arm AR or the end effector EF, the angle of the robot arm AR with respect to a reference direction (for example, a horizontal plane), or the inclination angle of the end effector EF with respect to the robot arm AR. This operation information may include information of at least a part, for example, the movable range of the robot arm AR or the end effector EF in the 3D space, the position, velocity, or acceleration of the robot arm AR during the operation of the robot arm AR, or the position, velocity, or acceleration of the end effector EF relative to the robot arm AR during the operation of the end effector EF.

In kinematics, not only the movable range of one robot arm but also the movable range of another robot arm are regulated. Accordingly, the surgical robot 300 operates based on the kinematics of each robot arm AR of the surgical robot 300, and therefore, interference between the plurality of robot arms AR during operation can be avoided.

The port position processing unit 164 acquires information of the surgical procedure. The surgical procedure refers to the procedure of surgery on the subject PS. The surgical procedure may be designated via the UI 120. Each treatment in robotic surgery may be determined depending on the surgical procedure. Depending on the treatment, the end effector EF required for the treatment may be determined. Accordingly, the end effector EF mounted on the robot arm AR may be determined depending on the surgical procedure, and the type of the end effector EF mounted on the robot arm AR may be determined depending on the surgical procedure. In addition, a minimum region that is required for the treatment or a recommended region that is recommended to be secured for the treatment may be determined depending on the treatment.

The port position processing unit 164 acquires information of a target region. The target region may be a region including targets (for example, tissues (such as blood vessels, bronchial tubes, organs, bones, brain, heart, feet, and neck) to be treated by robotic surgery. The tissues may broadly include tissues of the subject PS such as diseased tissues, normal tissues, organs, and parts.

The port position processing unit 164 may acquire information regarding the position of the target region from the memory 150. The port position processing unit 164 may acquire the information of the position of the target region from the external server via the communication unit 110. The port position processing unit 164 may receive a designation of the position of the target region via the UI 120 to acquire the information regarding the position of the target region.

The port position processing unit 164 may execute a port position simulation. The port position simulation may be a simulation in which the user operates the UI 120 to determine whether or not desired robotic surgery can be performed on the subject PS. In the port position simulation, while simulating surgery, the user may operate the end effector EF inserted into each of the port positions in a virtual space to determine whether or not the target region as a surgery target is accessible. That is, in the port position simulation, while receiving the manual operation of the surgical robot 300, the user may determine whether or not a moving part (for example, the robot arm AR and the end effector EF) of the surgical robot 300 relating to robotic surgery is accessible to the target region as a surgery target without a problem. The port position processing unit 164 may obtain port position planning information through the port position simulation.

In the port position simulation, whether or not the target region is accessible may be determined based on the volume data of the subject PS, the acquired combination of the plurality of port positions, the kinematics of the surgical robot 300, the surgical procedure, the volume data of the virtual pneumoperitoneum state, and the like. While changing the plurality of port positions on the body surface of the subject PS, the port position processing unit 164 may determine whether or not the target region is accessible at each port position or may sequentially perform the port position simulation. The port position processing unit 164 may designate information regarding a finally preferable (for example, optimal) combination of port positions according to the user input via the UI 120. As a result, the port position processing unit 164 may plan the plurality of port positions to be pierced. The details of the port position simulation will be described below.

Using the plurality of port positions provided on the body surface of the subject PS, the port position processing unit 164 may derive (for example, calculate) a port position score representing the appropriateness for robotic surgery. That is, the port position score based on the combination of the plurality of port positions indicates the value of the combination of the plurality of port positions for robotic surgery. The port position score may be calculated based on the combination of the plurality of port positions, the kinematics of the surgical robot 300, the surgical procedure, the volume data of the virtual pneumoperitoneum state, and the like. The port position score is derived for each port position. The details of the port position score will be described below.

The port position processing unit 164 may adjust the port position based on the port position score. In this case, the port position processing unit 164 may adjust the port position based on the variation of the port position score according to the movement of the port position. The details of the port position adjustment will be described below.

As described above, the port position processing unit 164 may derive the plurality of port positions to be pierced according to the port position simulation. In addition, the port position processing unit 164 may derive the plurality of port positions to be pierced based on the port position score.

The display controller 166 causes the display 130 to display various data, information, or images. The display controller 166 may display the 3D image or the 2D image generated by the image generator 162. The display controller 166 may display an image showing the information of the plurality of ports PT (for example, the information of the port positions) generated by the image generator 162.

The display controller 166 may display an image showing the information of remaining ports (for example, the information of the port positions) other than a pre-pierced port PT1, which is a port PT that is previously pierced, among the plurality of ports PT generated by the image generator 162. In this case, the display controller 166 may display the image showing the plurality of port positions or the image showing the remaining port positions to superimpose the 3D image or the 2D image. The remaining ports may be ports (non-pierced ports) that have been not yet pierced.

The projection controller 167 controls the projection of the visible light from the projection unit 170. The projection controller 167 may control, for example, a frequency or an intensity of the visible light, a position to which the visible light is projected, or a timing at which the visible light is projected.

The projection controller 167 causes the projection unit 170 to project the visible light to the subject PS and displays various information on the body surface of the subject PS (for example, the body surface of the abdomen). The projection controller 167 may project laser light to the body surface of the subject PS to mark a specific position on the body surface. The specific position may be, for example, the port position to be pierced or a position on the volume data where the observation target (for example, the affected part) is present when shifted from the specific position on the body surface in the normal direction. That is, the projection controller 167 may be a laser pointer indicating the port position.

In addition, the projection controller 167 may cause the projection unit 170 to project the visible light to the body surface of the subject PS to superimpose and display information assistant robotic surgery (for example, the information regarding the port position) on the body surface of the subject PS. The superimposing information may be, for example, character information or graphic information. That is, the projection controller 167 may assist the user in robotic surgery using an augmented reality (AR) technique.

Figure 4:
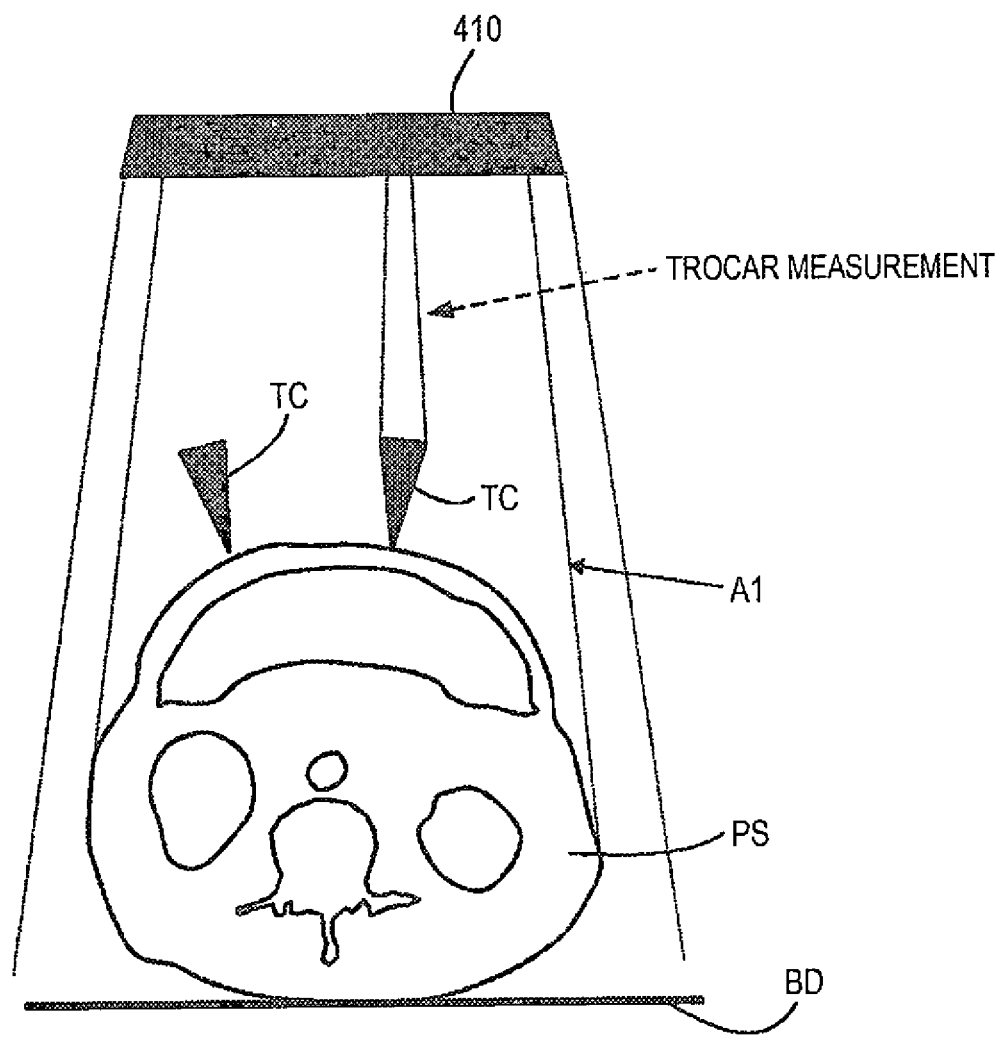
FIG. 4 is a view illustrating a measurement example of a port position of a pre-pierced port.

FIG. 4 is a view illustrating a measurement example of a port position of the pre-pierced port PT1. The measurement of the port position may be the 3D measurement. In FIG. 4, the subject PS (for example, a patient) is horizontally placed on a bed BD.

The depth sensor 410 may include: a light-emitting portion that emits infrared light; a light-receiving portion that receives infrared light; and a camera that captures an image. The depth sensor 410 may detect the distance from the depth sensor 410 to the subject PS based on the infrared light that is emitted from the light-emitting portion to the subject PS and reflected light that is reflected from the subject PS and received by the light-receiving portion. The depth sensor 410 may detect the upper, lower, left, and right sides of an object using the image captured by the camera. As a result, the depth sensor 410 may acquire information of a 3D position (3D coordinates) of each position (for example, the port position of the pre-pierced port PT1) on the body surface of the subject PS.

The depth sensor 410 may include a processor and an internal memory. The internal memory may store information regarding the shape of the trocar TC. Referring to the shape information of the trocar TC stored in the internal memory, the depth sensor 410 may detect (recognize) the trocar TC provided in the port PT pierced on the body surface of the subject PS to detect (measure) a 3D position of the trocar TC.

In addition, a predetermined mark may be formed on a surface of the trocar TC. The depth sensor 410 may capture an image using the predetermined mark on the trocar TC as a feature point to detect (recognize) the trocar TC by image recognition. As a result, the depth sensor 410 can improve the recognition accuracy of the trocar TC and can improve the measurement accuracy of the 3D position of the trocar TC.

In addition, the depth sensor 410 may include a stereo camera instead of the infrared sensor (the light-emitting portion and the light-receiving portion) such that the 3D position of the trocar TC can be measured by image processing. In this case, the depth sensor 410 may measure the 3D position of the trocar TC by recognizing the trocar TC by object recognition in an image captured by a stereo camera, detecting (recognizing) the position of the trocar TC on the body surface of the subject, and calculating the distance to the trocar TC.

The depth sensor 410 may measure each position or the position of the trocar TC on the body surface of the subject PS in a range that can be reached by the infrared light emitted from the infrared sensor or in a range where an image can be captured by the camera (refer to a range A1 in FIG. 4).

The deformation simulator 163 of the robotically-assisted surgical device 100 may acquire information regarding each position on the body surface of the subject PS in the actual pneumoperitoneum state, that is, information regarding the shape of the body surface of the subject PS in the actual pneumoperitoneum state from the depth sensor 410. In addition, the deformation simulator 163 may extract the contour (corresponding to the body surface) of the subject PS based on the volume data of the subject PS in the non-pneumoperitoneum state to acquire information regarding each position on the body surface of the subject PS in the non-pneumoperitoneum state, that is, information regarding the shape of the body surface of the subject PS in the non-pneumoperitoneum state.

The deformation simulator 163 may calculate a difference between each position on the body surface of the subject PS in the actual pneumoperitoneum state and each position on the body surface of the subject PS in the non-pneumoperitoneum state, that is, a difference between the shape of the body surface of the subject PS in the actual pneumoperitoneum state and the shape of the body surface of the subject PS in the non-pneumoperitoneum state. As a result, the deformation simulator 163 can recognize the amount of pneumoperitoneum for allowing the actual pneumoperitoneum state of the subject PS.

In addition, the deformation simulator 163 may correct a simulation method or a simulation result of the pneumoperitoneum simulation based on the difference between the actual pneumoperitoneum state and the virtual pneumoperitoneum state in the pneumoperitoneum simulation. That is, the deformation simulator 163 may correct a simulation method or a simulation result of the pneumoperitoneum simulation based on the actual amount of pneumoperitoneum. The deformation simulator 163 may store the correction information in the memory 150. In addition, the deformation simulator 163 may receive the amount of scavenging air from a pneumoperitoneum device via the communication unit 110 to correct a simulation method or a simulation result of the pneumoperitoneum simulation. As a result, the robotically-assisted surgical device 100 can improve the accuracy of the pneumoperitoneum simulation.

Next, an example of displaying a port position will be described.

The deformation simulator 163 performs the pneumoperitoneum simulation on the volume data obtained in the non-pneumoperitoneum state (for example, by preoperative CT scanning) to generate the volume data of the virtual pneumoperitoneum state. The image generator 162 may perform volume rendering on the volume data of the virtual pneumoperitoneum state to generate a volume rendering image. The image generator 162 may perform surface rendering on the volume data of the virtual pneumoperitoneum state to generate a surface rendering image.

The deformation simulator 163 may perform the pneumoperitoneum simulation on the volume data obtained in the non-pneumoperitoneum suite (for example, by preoperative CT scanning) to generate deformation information regarding deformation from the non-pneumoperitoneum state to the virtual pneumoperitoneum state. The image generator 162 may generate a surface from the volume data acquired in the non-pneumoperitoneum state (for example, by preoperative CT scanning) to generate a surface rendering image. The image generator 162 may apply the shape information to the surface generated from the volume data acquired in the non-pneumoperitoneum state (for example, by preoperative CT scanning) to generate a surface rendering image of the virtual pneumoperitoneum state.

The display controller 166 may cause the display 130 to visualize the 3D data (the volume rendering image or the surface rendering image of the virtual pneumoperitoneum state) with an annotation of the port position derived from the port position processing unit 164.

The projection controller 167 may project visible light to the port position on the body surface of the subject PS (for example, a patient) derived by the port position processing unit 164 to indicate the port position using the visible light and to visualize the port position. As a result, the user can perform a treatment such as piercing on the port position while checking the port position on the body surface of the subject PS.

The projection controller 167 may project visible light to the subject PS to display information regarding the port position on the body surface of the subject PS (for example, a patient) derived by the port position processing unit 164. In this case, the projection controller 167 may display the information regarding the port position (for example, the identification information of the port or an arrow indicating the port position) to superimpose the subject PS using an AR technique. As a result, referring to guide information by the visible light, the user can perform a treatment such as piercing on the port position while checking the information regarding the port position on the body surface of the subject PS.

Here, the deformation information will be described in detail.

The deformation simulator 163 detects movement (deformation) of each of the portions included in the volume data to generate the deformation information based on the plurality of volume data (CT images) obtained before and after pneumoperitoneum. In this case, the deformation simulator 163 performs movement analysis (deformation analysis) on the deformation of the plurality of volume data based on the plurality of volume data regarding the amount of pneumoperitoneum to acquire the deformation information in the volume data. A specific method of the deformation analysis is described in, for example, U.S. Pat. No. 8,311,300 and Japanese Patent No. 5408493 which are incorporated herein by reference. These methods are examples of non-rigid registration but may be rigid registration.

The deformation simulator 163 may acquire, as the deformation information, information regarding the amount of movement or information regarding the velocity at a given point of the volume data. When the method described in US2014/0148816A which is incorporated herein by reference is applied, the deformation simulator 163 separates the volume data into a 2D lattice node (k, l), and 2D coordinates (x, y) in a phase node (k, l, t) of a phase t of the 2D lattice is obtained. In this case, based on a difference between a plurality of nodes (k, l, t) obtained by changing the value of the phase t, the information regarding the amount of movement at the lattice point of the node (k, l) may be calculated. In addition, the deformation simulator 163 may differentiate the information regarding the amount of movement with time to calculate the information regarding the velocity. The information regarding the amount of movement or the velocity may be expressed by a vector.

When the deformation simulator 163 interpolates the deformation information of the 2D lattice at each point of the entire volume data, the deformation information of each point of the volume data can be obtained. When the deformation information of a predetermined point is applied to each point of a region including an observation site, the deformation information of each point of the region including the observation site can be obtained.

In addition, when the method described in Japanese Patent No. 5408493 is applied, the deformation simulator 163 may generate the deformation information based on volume data tk−1 and time information tk−1 thereof and volume data tk and time information tk thereof among the volume data (before and after pneumoperitoneum) aligned in time series. The deformation information may indicate information regarding a corresponding position on the plurality of volume data or correspondence of a corresponding object or information regarding the process of a change in the movement of the position and the object. A pixel of each volume data is an index indicating a position at any time between time k−1 and time k.

The deformation simulator 163 is not limited to the method of US2014/0148816A and may perform deformation analysis using another well-known registration method. The robotically-assisted surgical device 100 performs deformation analysis on each point or the observation site using the deformation information, and thus, the movement of any position in the subject before and after pneumoperitoneum can be grasped.

Next, a specific example of a standard port position will be described.

Figure 5A:
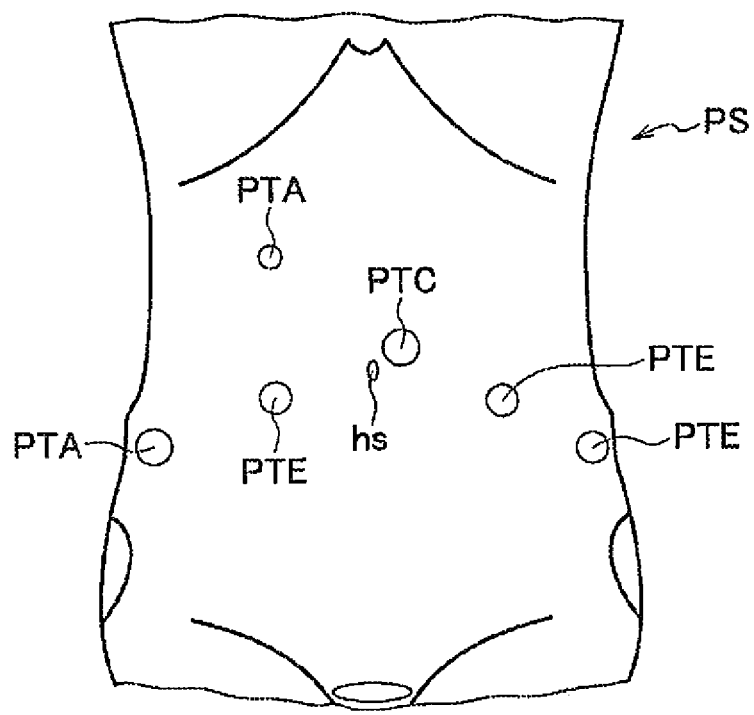
FIG. 5A is a view illustrating a first placement planning example of port positions placed on a body surface of a subject.
Figure 5B:
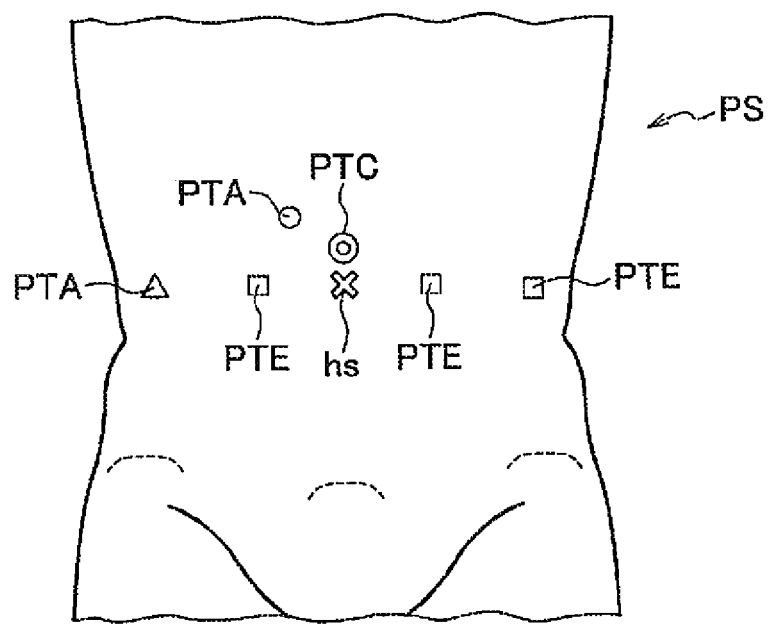
FIG. 5B is a view illustrating a second placement planning example of port positions placed on the body surface of the subject.
Figure 5C:
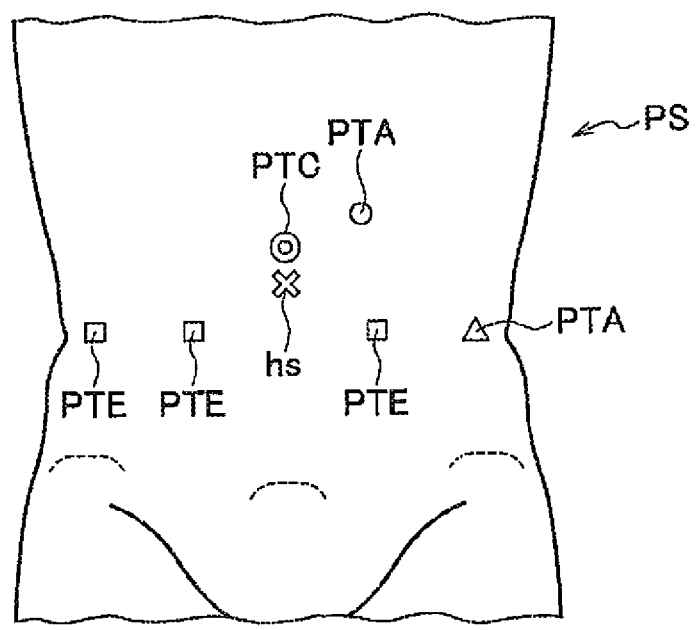
FIG. 5C is a view illustrating a third placement planning example of port positions placed on the body surface of the subject.

FIG. 5A is a view illustrating a first placement planning example of port positions placed on the body surface of the subject PS. FIG. 5B is a view illustrating a second placement planning example of port positions placed on the body surface of the subject PS. FIG. 5C is a view illustrating a third placement planning example of port positions placed on the body surface of the subject PS. The placement of a plurality of port positions may be planed, for example, according to the surgical procedure. In FIGS. 5A to 5C, the physical size of the subject PS or the position or size of a disease or the like of the observation target is not considered.

A plurality of port positions illustrated in FIGS. 5A to 5C are port positions that are planned to be pierced. There may be some errors between the port positions that are planned to be pierced and the port positions that are actually pierced. For example, there may be an error of about 25 mm.

The ports PT provided on the body surface of the subject PS may include a camera port PTC into which a camera CA is inserted, an end effector port PTE into which the end effector EF is inserted, and an auxiliary port PTA into which forceps held by an assistant are inserted. A plurality of ports PT may be present for each of the types (for example, for each of the camera port PTC, the end effector port PTE, and the auxiliary port PTA), or the sizes of the different types of ports PT may be the same as or different from each other. For example, the end effector port PT E into which the end effector EF for holding an organ or the end effector EF of which the movement in the subject PS is complex is inserted may be larger than the end effector port PTE into which the end effector EF as an electric knife is inserted. The placement position of the auxiliary port PTA may be planned relatively freely.

In FIG. 5A, large numbers of the end effector ports PTE and the auxiliary ports PTA are linearly arranged in the right direction of the subject PS and in the left direction of the subject PS, respectively, with respect to the port position of the camera port PTC as a reference (the vertex).

In FIG. 5B, large numbers of end effector ports PTE and the auxiliary ports PTA are linearly aligned with a position of a navel hs interposed therebetween. In addition, the camera port PTC is also placed near the navel hs.

In FIG. 5C, large numbers of end effector ports PTE and the auxiliary ports PTA are linearly aligned. The position of the navel hs is slightly shifted from the position on the straight line. In addition, the camera port PTC is also placed near the navel hs.

The reason why a large amount of ports PT are linearly placed in an existing plan is presumed to be that the user can easily recognize the port positions and feels safe. Among the plurality of ports PT, the camera port PTC may be placed at the center of the body surface of the subject PS.

Figure 6:
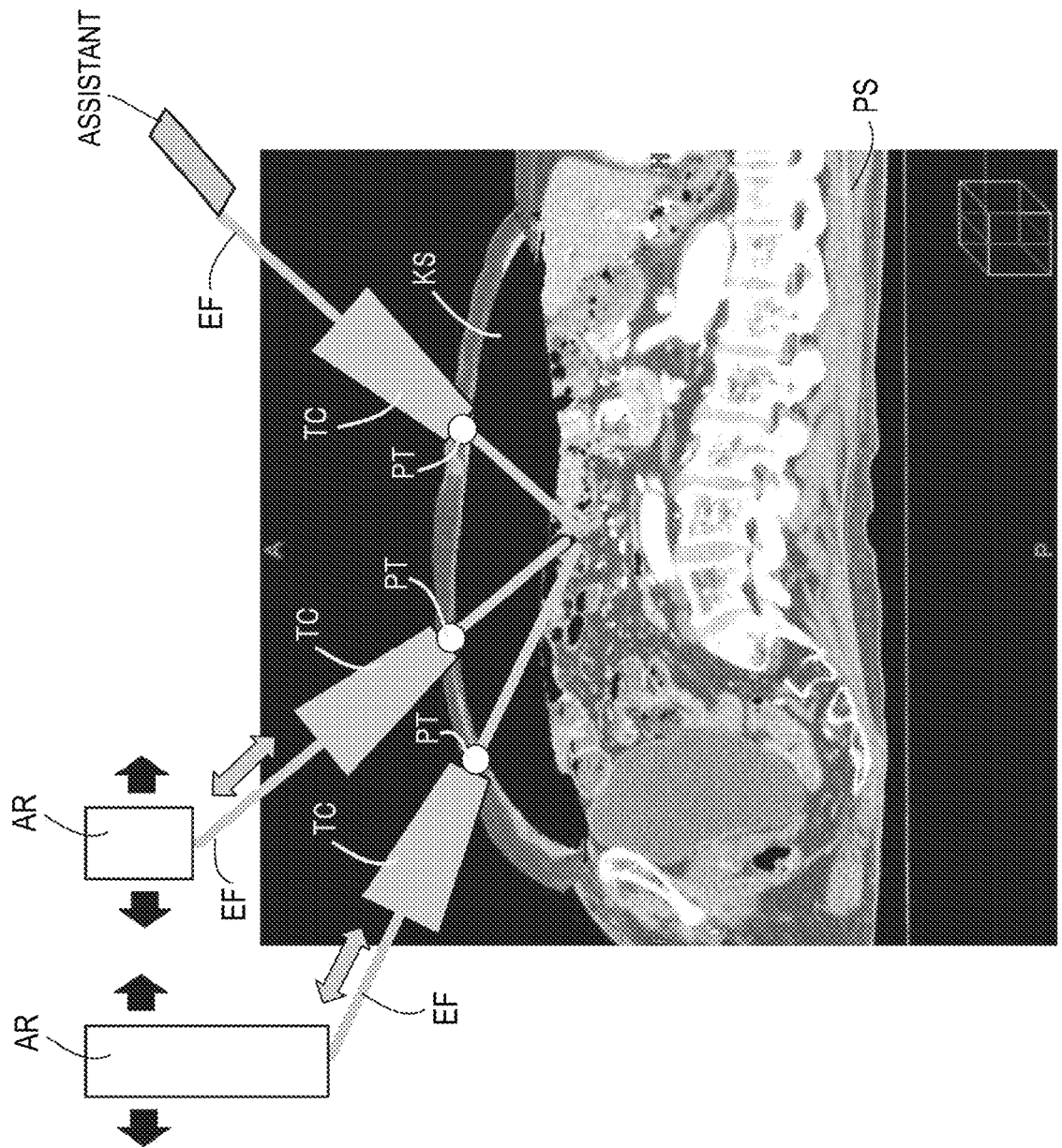
FIG. 6 is a view illustrating an example of a positional relationship between the subject, ports, trocars, and robot arms during robotic surgery.

FIG. 6 is a view illustrating an example of a positional relationship between the subject PS, the ports PT, the trocars TC, and the robot arms AR during robotic surgery.

In the subject PS, one or more ports PT are provided. In each of the ports PT, the trocar TC is placed. The end effector EF is connected (for example, is inserted) to the trocar TC and a work (treatment) can be performed using the end effector EF in the subject. The port position is disposed to be fixed and does not move during operation. Accordingly, the position of the trocar TC disposed at the port position does not also move. On the other hand, according to the treatment during operation, the robot arms AR and the end effectors are controlled based on the manipulation of the robot operation terminal, and the robot arms AR move. Accordingly, the positional relationship between the robot arms AR and the trocars TC changes, and the angles of the trocars TC with respect to the body surface of the subject or the angles of the end effectors EF attached to the trocars TC change. In FIG. 6, a monitor held by an assistant is also illustrated as an end effector.

Next, the operation of the robotically-assisted surgical device 100 will be described.

Figure 7:
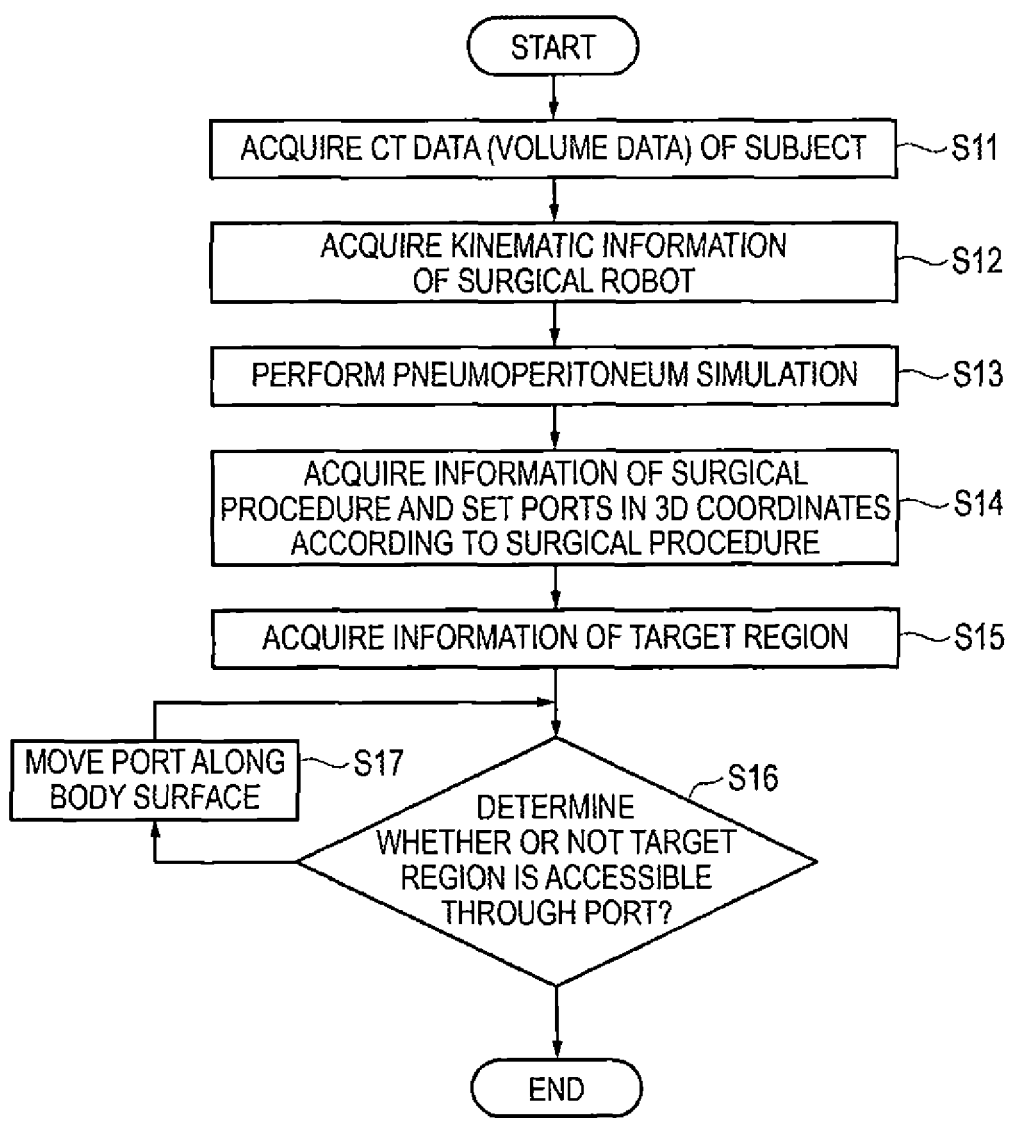
FIG. 7 is a flowchart illustrating an example of a procedure of a port position simulation by the robotically-assisted surgical device.

First, the procedure of the port position simulation will be described. FIG. 7 is a flowchart illustrating an example of the procedure of the port position simulation.

First, the port position processing unit 164 acquires the volume data including the subject PS, for example, via the communication unit 110 (S11). The port position processing unit 164 acquires the kinematic information from the surgical robot 300, for example, via the communication unit 110 (S12). The deformation simulator 163 performs the pneumoperitoneum simulation (S13) to generate the volume data of the virtual pneumoperitoneum state of the subject PS.

The port position processing unit 164 acquires the information of the surgical procedure (S14). The port position processing unit 164 acquires and sets the positions (initial positions) of the plurality of ports PT according to the acquired surgical procedure (S14). In this case, the port position processing unit 164 may set the positions of the plurality of ports PT in terms of 3D coordinates.

The port position processing unit 164 acquires the information of the target region (S15).

The port position processing unit 164 determines whether or not each of the end effectors EF inserted from each of the ports PT is accessible to the target region based on the positions of the plurality of ports acquired in S14 and the position of the target region (S16). Whether or not each of the end effectors EF is accessible to the target region may correspond to whether or not each of the end effectors EF can reach all the positions in the target region. That is, whether or not each of the end effectors EF is accessible to the target region shows that whether or not robotic surgery can be performed by the end effector EF (optionally, the plurality of end effectors EF) according to the acquired surgical procedure, and when each of the end effectors EF is accessible to the target region, robotic surgery can be performed.

When at least one of the end effectors EF is not accessible to at least a part of the target region, the port position processing unit 164 moves a port position of at least one port PT included in the plurality of ports PT to be pierced along the body surface of the subject PS (S17). In this case, the port position processing unit 164 may move the port position based on the user input via the UI 120. The port PT to be moved includes at least a port PT into which the end effector EF that is not accessible to at least a part of the target region is inserted.

When each of the end effectors EF is accessible to the target region, the processing unit 160 ends the process of the port position simulation of FIG. 7.

As described above, the robotically-assisted surgical device 100 performs the port position simulation such that whether or not each of the end effectors EF is accessible to the target region using the acquired plurality of port positions can be determined and thus whether or not robotic surgery can be performed by the surgical robot 300 using the acquired plurality of port positions can be determined. When the target region is not accessible using the plurality of port positions, at least a part of the port positions may be changed via the UI 120 to determine again whether or not the target region is accessible using the changed plurality of port positions. The robotically-assisted surgical device 100 can plan a combination of a plurality of port positions that are accessible to the target region as the plurality of port positions to be pierced. This way, the robotically-assisted surgical device 100 can plan the port position by the user manually adjusting the port position.

Next, an example of calculating the port position score will be described.

The plurality of port positions are determined, for example, according to the surgical procedure, and it may be assumed that each port position is disposed at any positions on the body surface of the subject PS. Accordingly, as the combination of the plurality of port positions, various combinations of port positions may be assumed. One end effector EF mounted on the robot arm AR can be inserted from one port PT into the subject PS. Accordingly, a plurality of end effectors EF mounted on a plurality of robot arms AR can be inserted from a plurality of ports PT into the subject PS.

A range where one end effector EF can reach the subject PS through the port PT is a working area (individual working area WA1) where a work (treatment in robotic surgery) can be performed by one end effector EF. Accordingly, an area where the individual working areas WA1 of the plurality of end effectors EF superimpose each other is a working area (entire working area WA2) where the plurality of end effectors EF can simultaneously reach the inside of the subject PS through the plurality of ports PT. In a treatment according to the surgical procedure, a predetermined number (for example, three) of end effectors EF needs to be operated at the same time. Therefore, the entire working area WA2 where the predetermined number of end effectors EF can simultaneously reach the inside of the subject PS is considered.

In addition, the position where the end effector EF can reach the subject PS varies depending on the kinematics of the surgical robot 300, and thus is added to the derivation of a port position as a position where the end effector EF is inserted into the subject PS. In addition, the position of the entire working area WA2 in the subject PS that is required to be secured varies depending on the surgical procedure, and thus is added to the derivation of a port position corresponding to the position of the entire working area WA2.

The port position processing unit 164 may calculate the port position score for each of the acquired (assumed) combinations of the plurality of port positions. The port position processing unit 164 may plan a combination of port positions having a port position score (for example, a maximum port score) that satisfies predetermined conditions among the assumed combinations of the plurality of port positions. That is, the plurality of port positions included in the planned combination of the port positions may be planned as the plurality of port positions to be pierced.

A relationship between the port position and the operation of the moving part of the surgical robot 300 may satisfy a relationship described in, for example, Mitsuhiro Hayashibe, Naoki Suzuki, Makoto Hashizume, Kozo Konishi, Asaki Hattori, "Robotic surgery setup simulation with the integration of inverse-kinematics computation and medical imaging", computer methods and programs in biomedicine, 2006, P63-P72 and Pal Johan From, "On the Kinematics of Robotic-assisted Minimally Invasive Surgery", Modeling Identification and Control, Vol. 34, No. 2, 2013, P69-P82, which is incorporated herein by reference.

Figure 8:
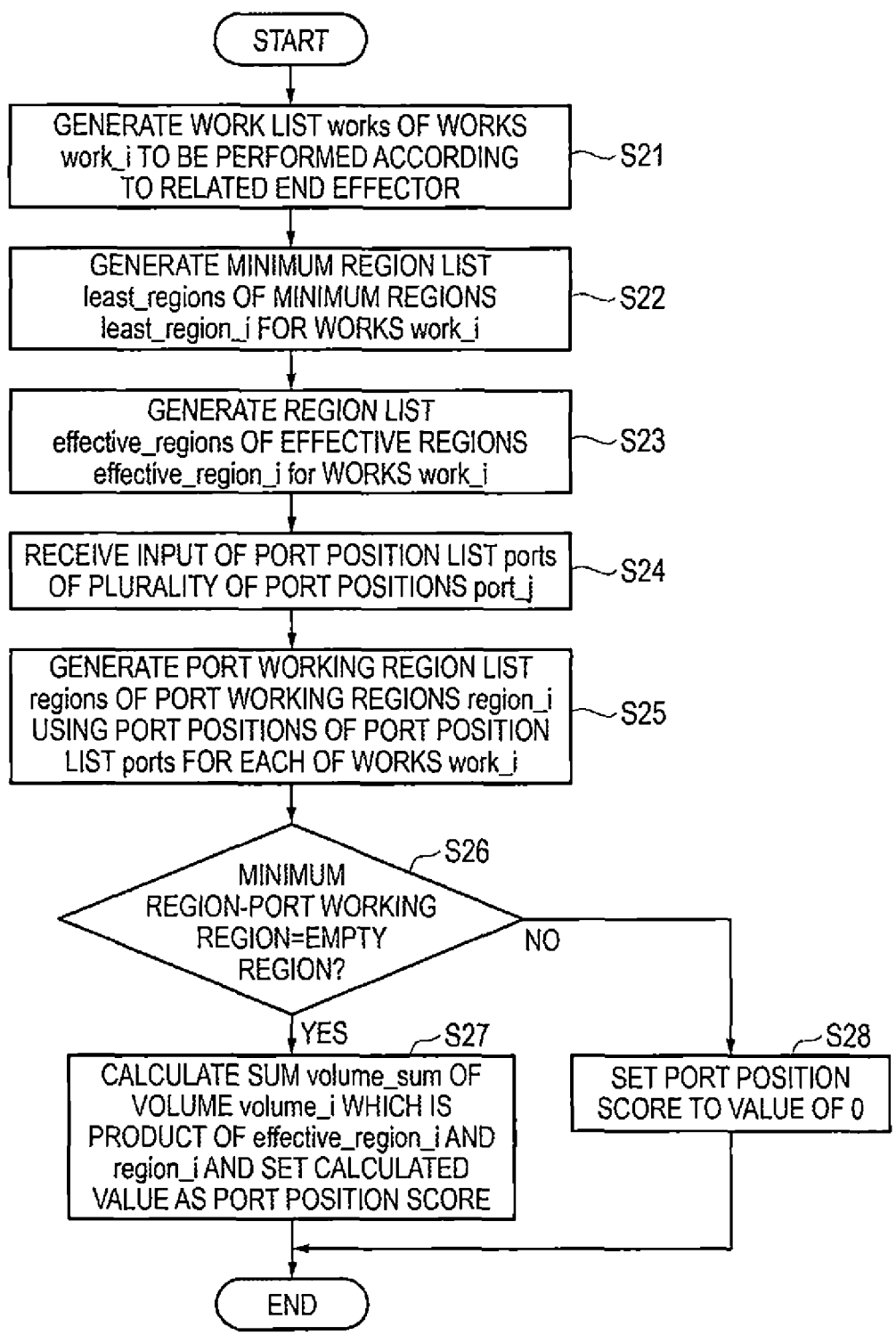
FIG. 8 is a flowchart illustrating an operation example when a port position score is calculated by the robotically-assisted surgical device.

FIG. 8 is a flowchart illustrating an operation example when the port position score is calculated by the robotically-assisted surgical device 100.

Before the process of FIG. 8, the acquisition of the volume data of the subject PS, the acquisition of the kinematic information of the surgical robot 300, the execution of the pneumoperitoneum simulation, and the acquisition of the information of the surgical procedure are performed in advance as in S11 to S14 of the port position simulation illustrated in FIG. 8. In addition, the kinematic information may include the information of each of the end effectors EF mounted on each robot arm according to the surgical procedure. The initial value of the port position score is 0. The port position score is an evaluation function (evaluation value) indicating the value of the combination of the port positions. A variable i is an example of identification information of a work, and a variable j is an example of identification information of a port.

The port position processing unit 164 generates a work list works, which is a list of works work_i in which each end effector EF is used, according to the surgical procedure (S21). The work work_i includes information for allowing each end effector EF to perform the work in the surgical procedure according to the surgical procedure. The work work_i may include, for example, gripping, dissection, or suture. The work may include a solo work that is performed by a single end effector EF or a cooperative work that is performed by a plurality of end effectors EF.

Based on the surgical procedure and the volume data of the virtual pneumoperitoneum state, the port position processing unit 164 plans a minimum region least_region_i, which is a region necessary for performing the works work_i included in the work list works (S22). The minimum region may be specified as a 3D region in the subject PS. The port position processing unit 164 generates a minimum region list least_regions, which is a list of the minimum regions least_region_i (S22).

Based on the surgical procedure, the kinematics of the surgical robot 300, and the volume data of the virtual pneumoperitoneum state, the port position processing unit 164 plans an effective region effective_region_i that is recommended for performing the work work_i included in the work list works (S23). The port position processing unit 164 generates an effective region list effective_regions, which is a list of the recommended regions effective_region_i (S23). The recommended region may include not only the minimum space (minimum region) for performing the work but also a space that is effective, for example, the end effector EF to operate.

The port position processing unit 164 acquires information of a port position list ports, which is a list of a plurality of port positions port_j (S24). The port position may be specified by 3D coordinates (x, y, z). The port position processing unit 164 may receive, for example, a user input through the UI 120 to acquire the port position list ports including one or more port positions designated by the user.

The port position processing unit 164 may acquire the port position list ports that are stored in the memory 150 as a template.

Based on the surgical procedure, the kinematics of the surgical robot 300, the volume data of the virtual pneumoperitoneum state, and the acquired plurality of port positions, the port position processing unit 164 plans a port working region region_i, which is a region where each of the end effectors EF can perform each of the works work_i through each of the port positions port_j (S25). The port working region may be specified as a 3D region. The port position processing unit 164 generates a port working region list regions, which is a list of the port working regions region_i (S25).

The port position processing unit 164 subtracts the port working region region_i from the minimum region least_region_i for each of the works work_i to calculate a subtracted region (subtracted value) (S26). The port position processing unit 164 determines whether or not the subtracted region is an empty region (the subtracted value is negative) (S26). Whether or not the subtracted region is an empty region shows that whether or not a region that is not covered with the port working region region_i (a region that cannot be reached by the end effector EF through the port PT) is present in at least a part of the minimum region least_region_i.

When the subtracted region is an empty region, the port position processing unit 164 calculates a volume value volume_i, which is the product of the recommended region effective_region_i and the port working region region_i (S27). The port position processing unit 164 sums the volume values volume_i calculated for each of the works work_i to calculate a sum value volume_sum. The port position processing unit 164 sets the sum value volume_sum as the port position score (S27).

That is when the subtracted region is an empty region, it is preferable that the region that is not covered with the port working region is not present in the minimum region and this port position list ports (the combination of the port positions port_j) is selected. Therefore, in order to promote the selection of the port position list, the value for each of the works work_i is added to the port position score. In addition, by planning the port position score based on the volume value volume_i, as the minimum region or the port working region increases, the port position score increases, and tins port position list ports is more likely to be selected. Accordingly, the port position processing unit 164 is more likely to select a combination of port positions in which the minimum region or the port working region is large and each treatment is easy in surgery.

On the other hand, when the subtracted region is not an empty region, the port position processing unit 164 sets the port position score of the port position list ports to a value of 0 (S28). That is, since the region that is not covered with the port working region is present in at least a part of the minimum region and the work of the target work work_i may not be completed, it is not preferable to select this port position list ports. Thus, in order to make the selection of the port position list ports difficult, the port position processing unit 164 sets the port position score to a value of 0 and excludes the port position list from candidates of the selection. In this case, when the subtracted region is an empty region in a case where another work work_i is performed using the same port position list ports, the port position processing unit 164 sets the port position score to a value of 0 as a whole.

The port position processing unit 164 may calculate a port position score for all the works work_i by repeating the respective steps of FIG. 8 for all the works work_i.

As described above, the robotically-assisted surgical device 100 derives the port position score, and when the robotic surgery is performed using the plurality of port positions provided on the body surface of the subject PS, the appropriateness of the combination of the port positions to be pierced can be grasped. The individual working area WA1 and the entire working area WA2 depend on the placement positions of the plurality of ports to be pierced. Even in this case, by using a score (port position score) for each combination of a plurality of port positions, the surgical robot 300 can derive a combination of a plurality of port positions in which, for example, the port position score is a threshold th1 or higher (for example, maximum), and the port positions with which robotic surgery can be easily performed can be set.

In addition, by appropriately securing the working area based on the port position score, the user can secure a wide visual field in the subject that cannot be directly visually observed in robotic surgery, a wide port working region can be secured, and unexpected events can be easily handled.

In addition, in robotic surgery, the port positions to be pierced are not variable. However, the robot rums AR on which the end effectors inserted into the port positions are mounted are movable in a predetermined range. Therefore, in robotic surgery, depending on the planned port positions, the robot arms AR may interfere with each other. Therefore, port position planning is important. In addition, the positional relationship between the surgical robot 300 and the subject PS cannot be changed during operation in principle. Therefore, port position planning is important.

Figure 9:
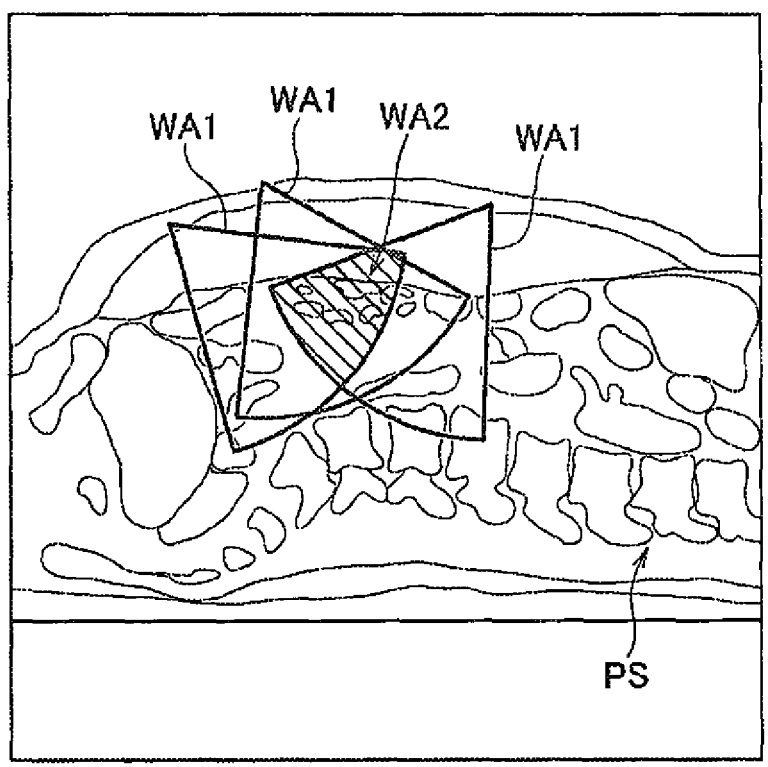
FIG. 9 is a view illustrating an example of working areas determined based on port positions.

FIG. 9 is a view illustrating an example of working areas determined based on the port positions. The individual working area WA1 is an individual working area corresponding to each of the port positions port_j. The individual working area WA1 may be a region in the subject PS that can be reached by each of the end effectors EF. An area where the respective individual working areas WA1 superimpose each other is the entire working area WA2. The entire working area WA2 may correspond to the port working region region_i. The robotically-assisted surgical device 100 can optimize each of the port positions using the port position score, and the suitable individual working areas WA1 and the suitable entire working area WA2 can be derived.

Next, the details of the port position adjustment will be described.

The port position processing unit 164 acquires information of the plurality of port positions (candidate positions), for example, based on the template stored in the memory 150 or the user instruction via UI 120. The port position processing unit 164 calculates the port position score for the case using the plurality of port positions based on the acquired combination of the plurality of port positions.

The port position processing unit 164 may adjust the position of the port PT based on the port position score. In this case, the port position processing unit 164 may adjust the position of the port PT based on the port position score for the acquired plurality of port positions and the port position score obtained when at least one port position among the plurality of port positions is changed. In this case, the port position processing unit 164 may also consider a small movement or a differential of the port position in each of the directions (x direction, y direction, and z direction) in a 3D space.

The x direction may be a direction along a left-right direction with respect to the subject PS. The y direction may be a forward-backward direction (thickness direction of the subject PS) with respect to the subject PS. The z direction may be an up-down direction (body axis direction of the subject PS) with respect to the subject PS. The x direction, the y direction, and the z direction may be three directions defined by Digital Imaging and Communications in Medicine (DICOM). The x direction, the y direction, and the z direction may be directions other than the above-described directions and are not necessarily the directions with respect to the subject PS.

For example, the port position processing unit 164 may calculate a port position score F (ports) for the plurality of port positions according to (Expression 1) to calculate a differential value F' of F.

$$F(\text{port}\_j(x+\Delta x,y,z))-F(\text{port}\_j(x,y,z))$$

$$F(\text{port}\_j(x,y+\Delta y,z))-F(\text{port}\_j(x,y,z))$$

$$F(\text{port}\_j(x,y,z+\Delta z))-F(\text{port}\_j(x,y,z)) \quad \text{(Expression 1)}$$

That is, the port position processing unit 164 calculates the port position score F for the port position F (port_j(x+Δx, y, z)), calculates the port position score F for the port position F (port_j(x, y, z)), and calculates a difference therebetween. This difference value indicates a change in the port position score with respect to a small change of the port position F (port_j(x, y, z)) in the x direction, that is, the differential value F' of F in the x direction.

In addition, the port position processing unit 164 calculates the port position score F for the port position F (port_j(x, y+Δy, z)), calculates the port position score F for the port position F (port_j(x, y, z)), and calculates a difference therebetween. This difference value indicates a change in the port position score with respect to a small change of the port position F (port_j(x, y, z)) in the y direction, that is, the differential value F' of F in the y direction.

In addition, the port position processing unit 164 calculates the port position score F for the port position F (port_j(x, y, z+Δz)), calculates the port position score F for the port position F (port_j(x, y, z)), and calculates a difference therebetween. This difference value indicates a change in the port position score with respect to a small change of the port position F (port_j(x, y, z)) in the z direction, that is, the differential value F' of F in the z direction.

The port position processing unit 164 calculates a maximum value of the port position score based on the differential value F' of each of the directions. In this case, the port position processing unit 164 may calculate a port position having the maximum port position score according to the steepest descent method based on the differential value F'. The port position processing unit 164 may adjust the port position to optimize the port position such that the calculated port position is a position to be pierced. Instead of the port position in which the port position score is the maximum, the port position may be, for example, a position in which the port position score is the threshold th1 or higher as long as the port position score is improved (increases).

The port position processing unit 164 may apply this port position adjustment to the adjustment of another port position included in the combination of the plurality of port positions or to the adjustment of port positions of another combination of a plurality of port positions. As a result, the port position processing unit 164 can plan the plurality of ports PT of which the respective port positions are adjusted (for example, optimized) as the port positions to be pierced.

Regarding the plurality of port positions (coordinates of the port positions), there may be an error of about a predetermined length (for example, 25 mm) between a piercing-planned position and an actual piercing position, and it is presumed that a port position planning accuracy of 3 mm at most is sufficient. Therefore, the port position processing unit 164 may set a plurality of port positions included in the combination of port positions as piercing-planned positions per predetermined length of the body surface of the subject PS, and the port position score may be calculated for each of the plurality of port positions. That is, the piercing-planned positions may be placed in a lattice shape (grid) of the predetermined length (for example, 3 mm) on the body surface of the subject PS. In addition, when it is assumed that the number of ports (for example, the number of intersections in a lattice shape) on the body surface is n and the number of ports included in the combination of port positions is m, the port position processing unit 164 may combine by sequentially selecting m port positions from n port positions and may calculate the port position score for each of the combinations. This way, when the grid is not excessively small as in a lattice shape having an interval of 3 mm, the calculation load of the port position processing unit 164 can be inhibited from being excessive, and the port position scores of all the combinations can be calculated.

The port position processing unit 164 may adjust the plurality of port positions using a well-known method. The port position processing unit 164 may plan the port positions to be pierced as the plurality of port positions included in the adjusted combination of port positions. The well-known method of the port position adjustment may include techniques described in the followings: Shaun Selha, Pierre Dupont, Robert Howe, David Torchiana, "Dexterity optimization by port placement in robot-assisted minimally invasive surgery", SPIE International Symposium on Intelligent Systems and Advanced Manufacturing, Newton, Mass., 28-31, 2001; Zhi Li, Dejan Milutinovic, Jacob Rosen, "Design of a Multi-Arm Surgical Robotic System for Dexterous Manipulation", Journal of Mechanisms and Robotics, 2016; and US2007/0249911A, which are incorporated herein by reference.

Next, the port position adjustment using the pre-pierced port will be described.

When a plurality of ports are planned to be pierced, the port position processing unit 164 may acquire information (measurement information) regarding the port position of the pre-pierced port PT1 that is previously pierced (for example, pierced firstly). The port position processing unit 164 may plan a port position of a port that is to be pierced next (for example, pierced secondly) based on the port position of the pre-pierced port PT 1. As a result, even when there is a difference between the position of the port PT that is planned to be pierced and the position of the pre-pierced port PT1 that is actually pierced, the robotically-assisted surgical device 100 can change the port position of the port that is to be pierced next.

Figure 10:
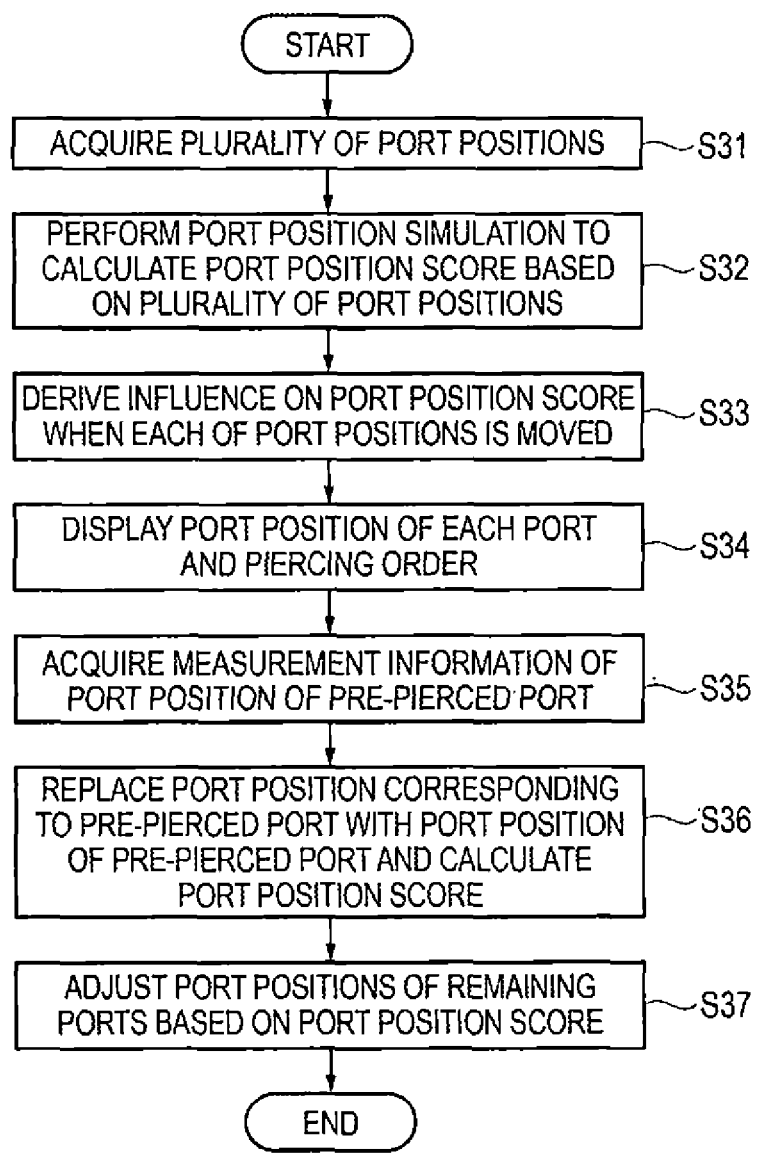
FIG. 10 is a flowchart illustrating an example of a port position adjustment procedure using the pre-pierced port by the robotically-assisted surgical device.

FIG. 10 is a flowchart illustrating an example of a port position adjustment procedure using the pre-pierced port PT1 by the robotically-assisted surgical device 100. In FIG. 10, the acquisition of the volume data of the subject PS, the acquisition of the kinematic information of the surgical robot 300, the execution of the pneumoperitoneum simulation, and the acquisition of the information of the surgical procedure are performed in advance as illustrated in FIG. 8.

The port position processing unit 164 acquires information of a plurality of port positions (positions of piercing candidates) (S31). The port position processing unit 164 performs the port position simulation to calculate the port position score based on the acquired plurality of port positions (S32). In this case, the port position processing unit 164 may calculate the port position score based on the surgical procedure, the kinematics of the surgical robot 300, the volume data of the virtual pneumoperitoneum state, and the acquired plurality of port positions.

The port position processing unit 164 calculates influence on the port position score when each port position is temporarily moved (S33). In this case, the port position processing unit 164 may calculate, as the influence, an amount of the change (for example, a decrease) in port position score when the port position is moved by a predetermined distance (for example, a small distance). The amount of the change in port position score when the port position is moved by the predetermined distance may be calculated according to (Expression 1) above, that is, may correspond to the differential value F' of the port position score F.

The port position processing unit 164 plans the piercing order of the ports PT such that the ports PT are pierced in order from the port PT having the highest influence. The display controller 166 or the projection controller 167 may display information regarding the position of each port PT and the piercing order (S34). As a result, the user (for example, an operator or an assistant) can easily recognize the planned port positions and can also easily recognize the piercing order in consideration of the influence.

For example, the piercing order may match the descending order of the influence. However, the piercing order may match the ascending order of the influence The influence corresponds to the amount of change in port position score when the port position is changed, and thus the influence can be also said as the degree of necessity of piercing accuracy. That is, it can be said that a port PT having a high influence is a port having a high degree of necessity of piercing accuracy, and it can be said that a port PT having a low influence is a port having a low degree of necessity of piercing accuracy. Accordingly, the display of the piercing order as the descending order of the influence can be said as an instruction to the user for piercing the ports in order from the port having the highest degree of necessity of piercing accuracy. Also, the display of the piercing order as the ascending order of the influence can be said as an instruction to the user for piercing the ports in order from the port having the lowest degree of necessity of piercing accuracy.

The user pierces the corresponding port at the planned port position. The user installs the trocar TC at the pierced port PT (pre-pierced port PT1). The measuring instrument 400 measures the port position of the pre-pierced port PT1. The port position of the pre-pierced port PT1 may be automatically measured using the trocar TC or the like and transmitted to the robotically-assisted surgical device 100, or may be manually measured and then the measurement result may be input via the UI 120. The port position processing unit 164 may acquire measurement information of the port position of the pre-pierced port PT1 via the communication unit 110 or the UI 120 (S35). In addition, the port position processing unit 164 may acquire identification information for identifying the pre-pierced port PT1 via the UI 120. As a result, the robotically-assisted surgical device 100 can identify the pierced port among the acquired positions of the plurality of ports.

The port position processing unit 164 replaces a port position of a piercing candidate corresponding to the pre-pierced port PT1 among the plurality of port positions acquired in S31 with the port position of the pre-pierced port PT1. Based on the plurality of port positions obtained by the replacement, the port position processing unit 164 calculates the port position score (the port position score in consideration of the pre-pierced port PT1) for the combination of the plurality of port positions obtained by the replacement (S36). In this case, the port position processing unit 164 may calculate the port position score based on the surgical procedure, the kinematics of the surgical robot 300, the volume data of the virtual pneumoperitoneum state, and the plurality of port positions obtained by the replacement.

The port position processing unit 164 adjusts and plans the remaining port positions based on the port position score in consideration of the pre-pierced port PT1 (S37). The port position processing unit 164 may perform the adjustment of the remaining port positions using the above-described method of the port position adjustment.

The port position of the pre-pierced port PT1 that is previously pierced is a fixed position, and the remaining port positions that have been not yet pierced are variable positions. Therefore, the port position processing unit 164 proceeds to S31 after S37 and may freely change the remaining port positions among the plurality of port positions including the pre-pierced port PT1 to change the combination of the plurality of port positions. The process of FIG. 10 may be repeatedly performed on the changed combination of the plurality of port positions. The port position processing unit 164 may plan the remaining port positions so as to be a combination of a plurality of port positions in which, for example, the port position score is the threshold th1 or higher (for example, maximum). As a result, the appropriateness of the remaining port positions can be improved (for example, optimized) in consideration of the pre-pierced port PT1.

When the port position processing unit 164 derives the piercing order in S34 in the repeated process of FIG. 10, since the pre-pierced port PT1 is previously pierced, and the piercing order is fixed. Accordingly, here, the port position processing unit 164 derives the piercing order of the remaining ports.

According to the port position adjustment procedure using the pre-pierced port PT1, even when the port PT is pierced at a position misplaced from the piercing-planned position, the robotically-assisted surgical device 100 can adjust the remaining port positions in consideration of the port position of the pre-pierced port PT1. Accordingly, even when the operation efficiency or the safety of robotic surgery is likely to deteriorate with the derived combination of the plurality of port positions due to the error of the piercing position of the pre-pierced port PT1, deterioration in the operation efficiency and the safety can be suppressed by replacing the remaining port positions in consideration of the pre-pierced port PT1.

Figure 11A:
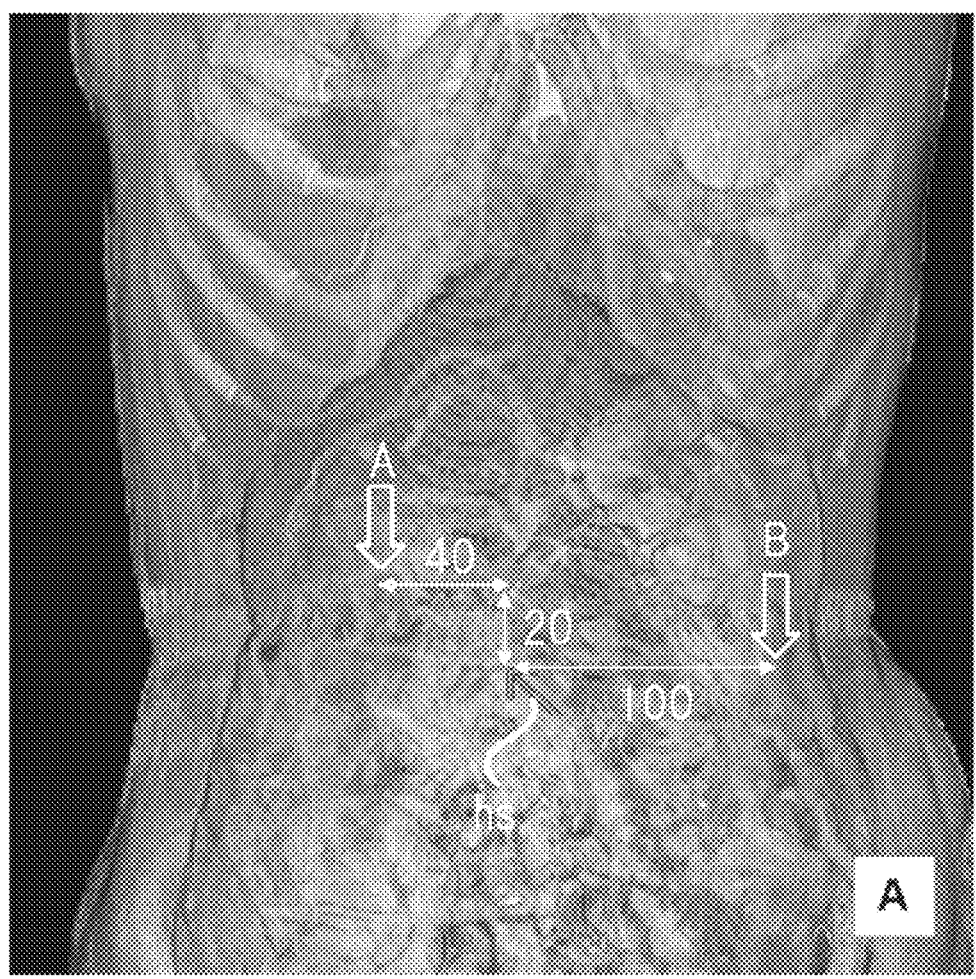
FIG. 11A is a view illustrating an image display example including a guide display before piercing a port.
Figure 11B:
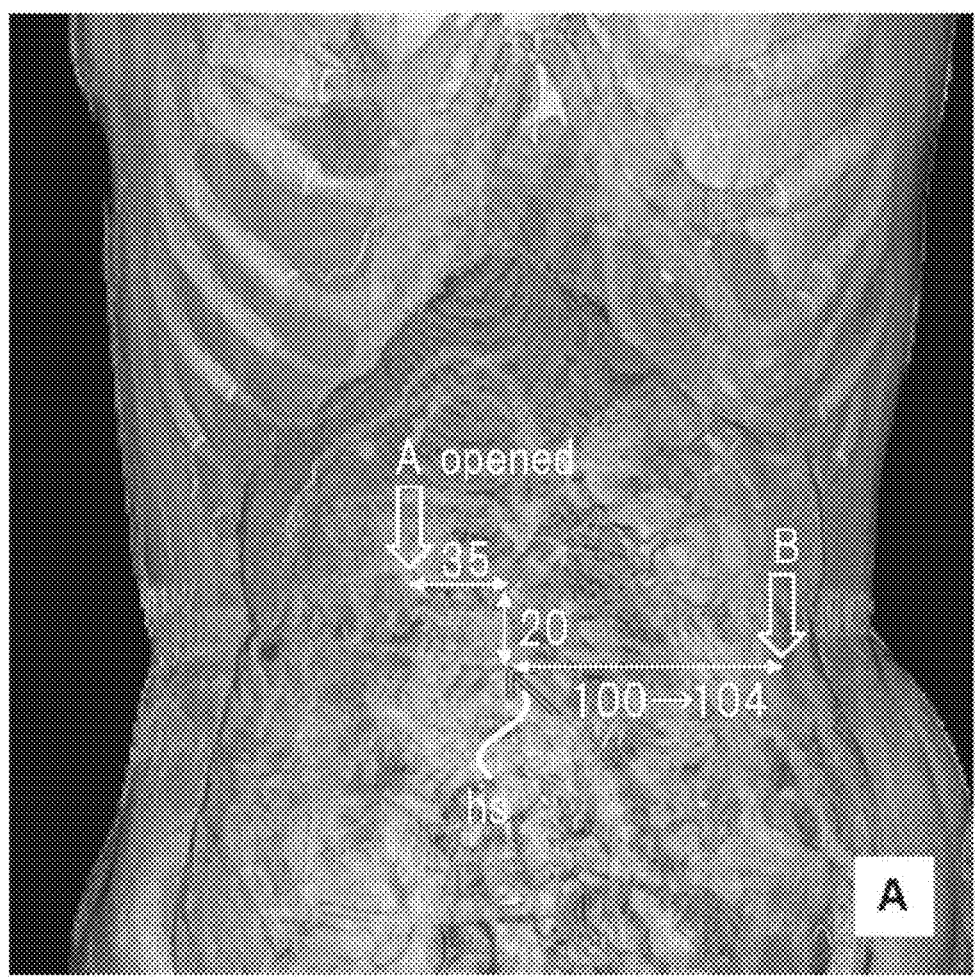
FIG. 11B is a view illustrating an image display example including a guide display after piercing the port.

FIG. 11A is a view illustrating an image display example including a guide display before piercing a port. FIG. 11B is a view illustrating an image display example including a guide display after piercing the port. This image is the example displayed in the display 130. However, guide information for piercing the port PT may project visible light from the projection unit 170 to the body surface of the subject PS to display the guide information using the visible light.

In FIG. 11A, the volume rendering image is displayed, and the guide information is also displayed to superimpose the volume rendering image. In the guide information, the presence of the port PT (port A) is shown at a head side of a large arrow, and identification information (for example, "A") of the port PT is shown in a tail side (base side) of the large arrow. In addition, in the guide information, a small arrow shows a distance between head positions of two direction arrows. In FIG. 11A, the distance is expressed in mm units. In addition, the position of the navel hs is also shown by an arrow.

In FIG. 11B, the volume rendering image is displayed, and the guide information is also displayed to superimpose the volume rendering image. In the guide information, the presence of the port PT (port A) is shown at a head side of a large arrow, and identification information (for example, "A") of the port is shown in a tail side (base side) of the large arrow. In addition, by adding "opened", it is shown that the port PT is the pre-pierced port PT1. For example, "opened A" shows that the port A is the pre-pierced port. In addition, in the guide information, a small arrow shows a distance between head positions of two direction arrows. In FIG. 11B, the distance is expressed in mm units. In addition, the position of the navel hs is also shown by an arrow.

Next, designation examples of port positions according to Comparative Example and the embodiment will be described.

Figure 12:
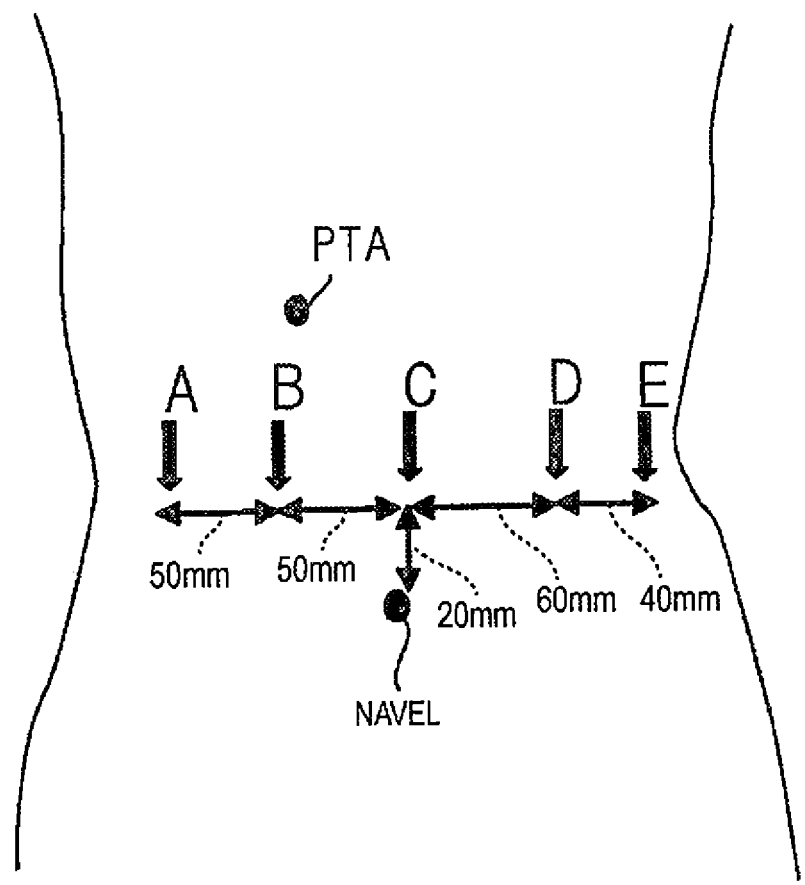
FIG. 12 is a view illustrating a designation example of port positions according to Comparative Example.

FIG. 12 is a view illustrating a designation example of port positions according to Comparative Example. As illustrated in FIG. 12, all the port positions to be pierced are determined before operation (before piercing the initial port). In FIG. 12, A, B, C, D, and E are examples of the identification information of the ports, and the lengths thereof are expressed in mm units. The respective values illustrated in FIG. 12 are merely exemplary and may be other values.

In FIG. 12, a port position of a port C is planned (designated) at a position moved from the navel hs to the head side in the body axis direction such that the distance between the navel hs and the port C becomes 20 mm. In addition, the ports A, B, C, D, and E are planned such that the ports A to E are linearly placed in a direction perpendicular to the body axis direction. That is, the ports A, B, C, D, and E are planned such that the distance between the port A and the port B is 50 mm, the distance between the port B and the port C is 50 mm, the distance between the port C and the port D is 60 mm, and the distance between the port D and the port E is 40 mm.

Figure 13:
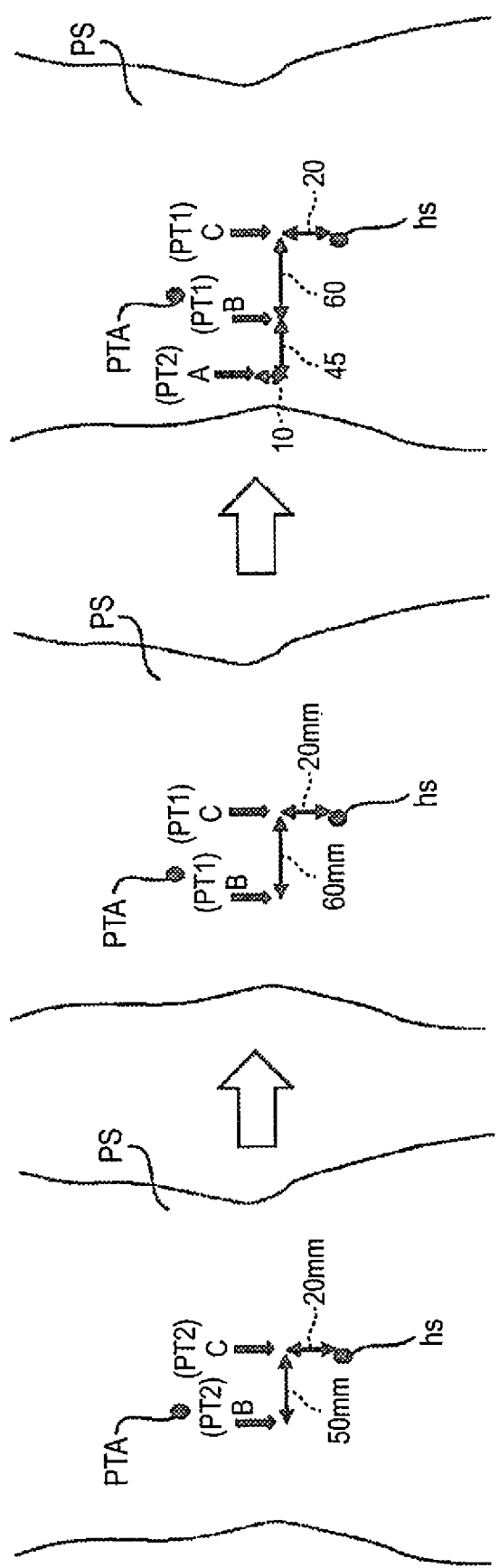
FIG. 13 is a view illustrating a designation example of port positions according to the first embodiment.

FIG. 13 is a view illustrating a designation example of port positions according to the present embodiment. In FIG. 13, "PT1" shows the pre-pierced port that is previously pierced, and "PT2" shows a non-pierced port that has been not yet pierced.

In FIG. 13, first, the positions of the ports A to E are planned, for example, before operation by the first simulation of port position or the first adjustment of port position. The positions are the same as the port positions planned in Comparative Example. That is, the port position of the port C is planned at a position moved from the navel hs to the head side in the body axis direction such that the distance between the navel hs and the port C becomes 20 mm. In addition, the port position of the port B is planned at a position moved from the navel hs in a direction perpendicular to the body axis direction such that the distance between the port B and the port C is 50 mm. For example, the planned port positions are pierced in order of the port C and the port B.

When the measuring instrument 400 measures the positions of the ports B and C that are actually pierced, the piercing position of the port C is the same as the planned port position. On the other hand, the piercing position of the port B is different from the planned port position, and the port B is pierced at a position moved from the navel hs in a direction perpendicular to the body axis direction such that the distance between the port B and the port C is 60 mm.

Regarding the above, the port position processing unit 164 performs the port position simulation or the port position adjustment again. Here, the port position adjustment is the port position adjustment using the pre-pierced port PT1. In this case, while the positions of the port C and the port B as the pre-pierced ports PT1 are fixed (fixed value) and the positions of the other ports A, D and E are set to be variable (variable values), each of the port positions is adjusted and planned. As a result of the port position simulation, in FIG. 13, the position of the port as the remaining port is changed from the original piercing-planned position (position planned by the first simulation of port position or the first adjustment of port position), and the port position is adjusted. That is, the port position of the port A is planned at a position at a distance of 45 mm from the port position of the port B in a direction (left direction in FIG. 13) perpendicular to the body axis direction and at a distance of 10 mm from the port position of the port B in a direction (upper direction in FIG. 13) along the body axis direction. That is, the port position processing unit 164 adjusts and plans the port position of the port A at a position in which the distance between the port A and the port B (the distance in the direction perpendicular to the body axis direction) is 45 mm and that is offset by 10 mm in the body axis direction.

Next, the variation of the port position adjustment using the pre-pierced port PT1 will be described.

The port position processing unit 164 may set a difficult-to-use region, which is a region where it is difficult to pierce a port on the body surface of the subject PS. The difficult-to-use region may include a region where it is difficult to provide a port, for example, due to medical history and adhesion or the like. The port position processing unit 164 may receive a user input via the UI 120 to designate the difficult-to-use region. Setting information of the difficult-to-use region may be stored in the memory 150 to be appropriately referred to. The port PT included in the difficult-to-use region is an inappropriate port to be inappropriate for the piercing the port PT. This inappropriate port may also be a non-pierced port or a pierced port. The port position processing unit 164 may prevent the port to be pierced from being provided in the difficult-to-use region or may allow the port to be pierced to be provided in the difficult-to-use region.

In addition, when the pre-pierced port PT1 is actually pierced and is difficult to use, the port position processing unit 164 may set a predetermined region including the pre-pierced port PT1 as the difficult-to-use region. The port position processing unit 164 may receive a user input via the UI 120 to acquire information indicating that the pre-pierced port PT1 is difficult to use. In this case, the pre-pierced port PT1 is an inappropriate port that is inappropriate for the piercing the port PT.

The port position processing unit 164 may reduce the priority of piercing of the port PT present in the difficult-to-use region such that the piercing order is planned to be the order from the highest priority. As a result, since the robotically-assisted surgical device 100 does not pierce the difficult-to-use region such as adhesion as long as possible, and attention can be paid not to damage the body surface of the subject PS corresponding to the difficult-to-use region foal is less likely to be used.

Conversely, the port position processing unit 164 may increase the priority of piercing of the port PT present in the difficult-to-use region such that the piercing order is planned to be the order from the highest priority. As a result, the robotically-assisted surgical device 100 tries to pierce the difficult-to-use region such as adhesion in an early stage. Therefore, the state of the difficult-to-use region can be checked in an early stage, and the next port piercing plan can be easily made.

Among the acquired or planned plurality of ports, the inappropriate port may be separated from ports (appropriate ports) other than the inappropriate port by a distance of a threshold th2 or more. As a result, when the appropriate port is pierced, the robotically-assisted surgical device 100 can reduce the influence of, for example, factors (for example, adhesion) that make the vicinity of the inappropriate port difficult to pierce.

The display controller 166 or the projection controller 167 may visualize the difficult-to-use region or the inappropriate port. That is, the display controller 166 may display an inappropriateness mark indicating the difficult-to-use region or the inappropriate port at a position corresponding to the difficult-to-use region or the inappropriate port in the rendering image based on the volume data. The projection controller 167 may project visible light to the difficult-to-use region on the body surface of the subject PS to display an inappropriateness mark indicating the difficult-to-use region. The display controller 166 or the projection controller 167 may display, as the inappropriateness mark, for example, "!" mark for displaying the port or a specific reason such as "possible adhesion" for the determination of the difficult-to-use region.

In the above-described example, the port position processing unit 164 derives the piercing order in consideration of the influence on the movement of a predetermined port itself. However, the port position processing unit 164 may derive (for example, calculate) the piercing order in consideration of influence (other influence) of other ports than the predetermined port. When the port position processing unit 164 adjusts the position of the predetermined port such that the distance between the predetermined port and other ports is a predetermined distance or less, the port position processing unit 164 may determine that the other influence is high and may increase or reduce the priority to derive the piercing order. In addition, when the port position processing unit 164 adjusts the position of the predetermined port such that the positions of the other ports are required to be adjusted and the working area also changes, the port position processing unit 164 may determine that the other influence is high and may increase or reduce the priority to derive the piercing order. As a result, by taking the other influence into consideration, the robotically-assisted surgical device 100 can suppress, for example, a change in the working area in which the other ports are used, that is, can suppress deterioration in the workability of robotic surgery in which the other ports are used. As a result, the workability of robotic surgery in which the predetermined port is used can be improved.

The port position processing unit 164 may plan the piercing order based on the piercing difficulty of the port PT. The piercing difficulty indicates the difficulty of piercing the port PT to be pierced. For example, as the distance from a reference position (for example, the navel h or another port) increases, the piercing difficulty may increase. That is, when the distance from the reference position to the port PT to be pierced is long, the distance is likely to deviate from the desired distance during the measurement of the distance. Therefore, it is difficult to pierce the port PT to be pierced. In addition, a port that is pierced through the side of the subject PS may have high piercing difficulty. The port position processing unit 164 may acquire information on the piercing difficulty stored in the memory 150.

The port position processing unit 164 may plan the piercing order of the ports PT such that the ports PT are pierced in order from the port having the highest piercing difficulty. The display controller 166 or the projection controller 167 may display information regarding the piercing order in consideration of the position of each port PT and the piercing difficulty. As a result, the user (for example, an operator or an assistant) can easily recognize the planned port positions and can also easily recognize the piercing order in consideration of the piercing difficulty.

After piercing a plurality of ports PT, the port position processing unit 164 may set the plurality of ports PT as the pre-pierced ports PT1 to adjust the remaining port positions to be pierced. In this case, by setting the port positions of the plurality of pre-pierced ports PT1 as fixed positions and setting the remaining port positions other than the plurality of pre-pierced ports PT1 as variable positions, the port position processing unit 164 may perform the port position simulation or the port position adjustment to adjust the remaining port positions. As a result, for example, a plurality of persons pierce the ports PT at the same time, the robotically-assisted surgical device 100 can adjust the remaining port positions in consideration of the piercing result of the plurality of pierced ports as the pre-pierced port PT1.

When the pre-pierced port PT1 is pierced, the deformation simulator 163 may acquire information on the position of the body surface of the subject PS in the actual pneumoperitoneum state from the measuring instrument 400 via the communication unit 110. The deformation simulator 163 may acquire information on the position of the body surface of the subject PS in the virtual pneumoperitoneum state that is obtained by performing the pneumoperitoneum simulation on the volume data of the subject PS in the non-pneumoperitoneum state. The deformation simulator 163 may correct the result of the pneumoperitoneum simulation to generate correction information for the correction based on a difference between the position of the body surface of the subject PS in the actual pneumoperitoneum state and the position of the body surface of the subject PS in the virtual pneumoperitoneum state.

Referring to the correction information, the port position processing unit 164 may perform the port position simulation or the port position adjustment based on the volume data of the virtual pneumoperitoneum state on which the corrected pneumoperitoneum simulation is performed. As a result, the robotically-assisted surgical device 100 can improve the adjustment accuracy of the port position adjustment using the pre-pierced port PT1.

Hereinbefore, various embodiments have been described with reference to the drawings. However, it is needless to say that the present disclosure is not limited to these examples. It is obvious to those skilled in the art that various changes or modifications can be conceived within the scope of the claims. Of course, it can be understood that these changes or modifications belong to the technical scope of the present disclosure In the first embodiment, the volume data as the captured CT images are transmitted from the CT apparatus 200 to the robotically-assisted surgical device 100. Instead, the volume data may be transmitted to a network server to temporarily accumulate the data and then stored in a server or the like. In this case, as necessary, the communication unit 110 of the robotically-assisted surgical device 100 may acquire the volume data from the server or the like via a wired circuit or a wireless circuit, or may acquire the volume data via any storage medium (not illustrated).

In the first embodiment, the volume data as the captured CT images are transmitted from the CT apparatus 200 to the robotically-assisted surgical device 100 via the communication unit 110. This example also includes a case where the CT apparatus 200 and the robotically-assisted surgical device 100 are substantially integrated into one product. In addition, the example may also include a case where the robotically-assisted surgical device 100 is considered as a console of the CT apparatus 200.

In the first embodiment, the CT apparatus 200 captures images to generate volume data including information regarding the inside of an organism. However, another device may capture images to generate volume data. Examples of the other device include a Magnetic Resonance imaging (MRI) device, a Positron Emission Tomography (PET) device, an angiographic device, and other modality devices. In addition, the PET device may be used in combination with other modality devices.

In the first embodiment, the surgical robot 300 is connected to the robotically-assisted surgical device 100. However, the surgical robot 300 is not necessarily connected to the robotically-assisted surgical device 100. The reason is for this is that this connection is not particularly limited as long as the kinematic information of the surgical robot 300 is acquired in advance. In addition, the surgical robot 300 may be connected after the end of the piercing of the ports. In addition, only a device that is a part of devices constituting the surgical robot 300 may be connected to the robotically-assisted surgical device 100. In addition, the robotically-assisted surgical device 100 itself may be a part of the surgical robot 300.

In the first embodiment, the surgical robot 300 is a surgical robot for minimal invasion. However, the surgical robot 300 for minimal invasion may be a surgical robot that assists laparoscopic surgery. In addition, the surgical robot 300 may be a surgical robot that assists endoscopic surgery.

In the first embodiment, the robotically-assisted surgical device 100 plans the port positions based on the volume data of the virtual pneumoperitoneum state of the subject, but the present disclosure is not limited thereto. For example, when the observation target is a respiratory organ or a cervical part, robotic surgery may be performed without pneumoperitoneum. That is, the robotically-assisted surgical device 100 may plan the port positions based on the volume data of the non-pneumoperitoneum state.

In the first embodiment, the subject PS is a human body but may be an animal body.

The present disclosure is also applicable to a program that implements the function of the robotically-assisted surgical device according to the first embodiment, in which the program is supplied to the robotically-assisted surgical device via a network or various storage media and is read and executed by a computer in the robotically-assisted surgical device.

As described above, the robotically-assisted surgical device 100 according to the embodiment assists minimally invasive robotic surgery by the surgical robot 300. The processing unit 160 may acquire 3D data of the subject PS (for example, the volume data of the non-pneumoperitoneum state or the volume data of the virtual pneumoperitoneum state). The processing unit 160 may acquire operation information (for example, kinematic information) regard to a moving part (for example, the robot arm AR or the end effector EF) of the surgical robot for performing the robotic surgery. The processing unit 160 may acquire information of a surgical procedure for operating the subject PS. The processing unit 160 may acquire position planning information for a plurality of ports PT that are to be pierced on a body surface of the subject PS. The processing unit 160 may acquire measurement information obtained by measuring the position of a first port (for example, the pre-pierced port PT1) that is pierced on the body surface of the subject PS among the plurality of ports PT. The processing unit 160 may determine a position of at least one of remaining ports other than the first port among the plurality of ports PT based on the measurement information of the position of the first port, the surgical procedure, the operation information (the kinematic information) of the surgical robot, and the 3D data. The processing unit 160 may display information indicating the determined position of the port in a display unit (for example, the display 130).

As a result, the robotically-assisted surgical device 100 can pierce the port PT while adjusting the port position during the piercing of the plurality of ports PT. For example, when the port PT is at a position that is difficult to pierce, it may be difficult to pierce the port at the originally planned position, and the port may be pierced at a position other than the planned position. Even in this case, the robotically-assisted surgical device 100 plans the remaining port positions (non-pierced ports) in consideration of the piercing position of the port PT (pre-pierced port) that is actually pierced such that a balance of the originally planned placement of the plurality of ports PT as a whole can be easily secured. Accordingly, the robotically-assisted surgical device 100 can reduce the influence of the misplacement of the first port from the piercing-planned position on robotic surgery.

In addition, the processing unit 160 may adjust positions of the plurality of ports PT including the first port and the remaining ports based on the acquired positions of the plurality of ports PT, the surgical procedure, the operation information of the surgical robot 300, and the 3D data. The processing unit 160 may readjust an adjusted position of at least one of the remaining ports among the plurality of ports based PT on the position of the pierced first port, the surgical procedure, the operation information of the surgical robot, and the 3D data.

As a result, the robotically-assisted surgical device 100 can adjust (for example, optimize) the placement of all the plurality of ports first and then can plan the placement suitable for all the plurality of ports. In addition, the robotically-assisted surgical device 100 can readjust the placement of the remaining ports in consideration of the piercing position of the first port that is actually pierced and then can plan the placement suitable for all the remaining ports. Accordingly, the robotically-assisted surgical device 100 can adjust each port position, for example, for each piercing and can optimize the position of a non-pierced port at each piercing timing.

In addition, the processing unit 160 may derive a priority (for example, the influence, the other influence, or the piercing difficulty) of piercing the remaining ports on the body surface of the subject PS. The processing unit 160 may plan the piercing order (an example of planning of the priority) for piercing the remaining ports based on the priority. The processing unit 160 may display information regarding the piercing order.

As a result, the user can recognize the desired piercing order for piercing the non-pierced ports. For example, the robotically-assisted surgical device 100 can increase the priority of a port in which the misplacement (error) of the piercing position has a high influence on the port positron score such that the ports can be promoted to be pierced in order from the port having the highest influence on the port positron score.

In addition, the processing unit 160 may designate, via the UI 120, an inappropriate port that is included in the plurality of ports PT and is inappropriate to be pierced. A distance between the inappropriate port and a port (appropriate port) that is not designated as the inappropriate port among the plurality of ports PT may be a threshold th2 or more.

As a result, the user can recognize the inappropriate port that is inappropriate as a target to be pierced. In addition, by setting the distance the inappropriate port and the appropriate port other than the inappropriate port to be within a predetermined distance, the influence of, for example, adhesion in the vicinity of the inappropriate port can be reduced during the piercing of the appropriate port.

In addition, the processing unit 160 may cause the display unit (for example, the display 130) to visualize the 3D data with an annotation of the information of the remaining ports (for example, the identification information of the remaining ports or the information of the port positions of the remaining ports) to superimpose the rendering image.

As a result, the user can recognize the positions of the remaining ports on the subject PS on the display unit. In addition, the robotically-assisted surgical device 100 uses the 3D data such that the user can estimate the influence of the piercing of the remaining ports on the inside of the subject PS.

In addition, the processing unit 160 may cause a projection unit 170 to project visible light representing information of the remaining ports to the body surface of the subject PS.

As a result, the robotically-assisted surgical device 100 can directly project the information of the remaining ports to the subject PS on which robotic surgery is performed. Therefore, the user can recognize the information (for example, the position information of the port, the identification information of the port, or the information of the piercing order of the port) of the remaining ports projected to the subject PS to be pierced. Accordingly, the user can pierce the port using the visible light on the subject PS as a mark. Accordingly, the robotically-assisted surgical device 100 can suppress misplacement of the actual piercing positions from the planned port positions of the remaining ports.

In addition, the processing unit 160 may perform a pneumoperitoneum simulation on volume data of the subject PS to generate the 3D data of a virtual pneumoperitoneum state.

As a result, for example, even when the actual pneumoperitoneum state is different from the pneumoperitoneum simulation state and the port is pierced at a position other than the planned position, the robotically-assisted surgical device 100 plans the remaining port positions (non-pierced ports) in consideration of the piercing position of the port PT (pre-pierced port) that is actually pierced, and a balance of the originally planned placement of the plurality of ports PT as a whole can be easily secured. Accordingly, in consideration of the state of pneumoperitoneum of the subject, live robotically-assisted surgical device 100 can reduce the influence of the misplacement of the first port from the piercing-planned position on robotic surgery.

The present disclosure is useful for, for example, a robotically-assisted surgical device capable of reducing the influence of misplacement of a pre-pierced port on robotic surgery, a robotically-assisted surgery method, and a program.

What is claimed is:

1. A robotically-assisted surgical device configured to assist minimally invasive robotic surgery with a surgical robot that includes a first robot arm holding a first surgical instrument, a second robot arm holding a second surgical instrument, and a third robot arm holding a third surgical instrument, at least one of the first surgical instrument, the second surgical instrument, and the third surgical instrument being an endoscope, the robotically-assisted surgical device comprising a processing unit and a display unit,
wherein
the processing unit is configured to:
acquire 3D data of a subject;
acquire kinematic information regard to the first robot arm, the second robot arm, and the third robot arm;
acquire information of a surgical procedure for operating the subject;
acquire position planning information for a plurality of ports which are to be pierced on a body surface of the subject and include a first port and remaining ports other than the first port, the position planning information including planned positions of the first port and the remaining ports, the first surgical instrument being inserted into the first port and the second surgical instrument and the third surgical instrument being respectively inserted into the remaining ports;
when the first port is pierced on the body surface and the remaining ports are not pierced on the body surface, acquire measurement information obtained by measuring a position of the first port which is pierced on the body surface;
determine a re-planned position of at least one of the remaining ports that are not pierced on the body surface, based on the position planning information including the planned position of the first port on the body surface, the measurement information of the position of the first port which is pierced on the body surface, the information of the surgical procedure, the kinematic information, and the 3D data; and
cause the display unit to display information indicating the determined re-planned position of the remaining ports.

2. The robotically-assisted surgical device according to claim 1, wherein the processing unit is configured to:
derive a priority of piercing the remaining ports on the body surface; and
cause the display unit to display information of piercing order regarding the priority.

3. The robotically-assisted surgical device according to claim 1, further comprising an operation unit, wherein
the processing unit is configured to designate, via the operation unit, an inappropriate port which is included in the plurality of ports and which is inappropriate to be pierced, and a distance between the inappropriate port and a port which is not designated as the inappropriate port among the plurality of ports is equal to or longer than a threshold.

4. The robotically-assisted surgical device according to claim 1, wherein the processing unit is configured to:
cause the display unit to visualize the 3D data with an annotation of the information of the remaining ports.

5. The robotically-assisted surgical device according to claim 1, wherein
the processing unit is configured to cause a projection unit to project visible light representing information of the remaining ports to the body surface.

6. The robotically-assisted surgical device according to claim 1, wherein
the processing unit is configured to perform a pneumoperitoneum simulation on volume data of the subject to generate the 3D data of a virtual pneumoperitoneum state.

7. The robotically-assisted surgical device according to claim 1, wherein the processing unit is further configured to:
cause the display unit to visualize the 3D data with an annotation of the information of the position of at least one of the remaining ports and the position planning information of the at least one of the remaining ports.

8. A robotically-assisted surgery method of a robotically-assisted surgical device configured to assist robotic surgery with a surgical robot that includes a first robot arm holding a first surgical instrument, a second robot arm holding a second surgical instrument, and a third robot arm holding a third surgical instrument, at least one of the first surgical instrument, the second surgical instrument, and the third surgical instrument being an endoscope, the robotically-assisted surgery method comprising:
acquiring 3D data of a subject;
acquiring kinematic information regard to the first robot arm, the second robot arm, and the third robot arm of the surgical robot for performing the robotic surgery;
acquiring information of a surgical procedure for operating the subject;
acquiring position planning information for a plurality of ports which are to be pierced on a body surface of the subject and include a first port and remaining ports other than the first port, the position planning information including planned positions of the first port and the remaining ports other than the first port, the first surgical instrument being inserted into the first port and the second surgical instrument and the third surgical instrument being respectively inserted into the remaining ports;
when the first port is pierced on the body surface and the remaining ports are not pierced on the body surface, acquiring measurement information obtained by measuring a position of the first port which is pierced on the body surface;
determining a re-planned position of at least one of the remaining ports that are not pierced on the body surface, based on the position planning information including the planned position of the first port on the body surface, the measurement information of the position of the first port which is pierced on the body surface, the information of the surgical procedure, the kinematic information, and the 3D data; and
causing a display unit to display information indicating the determined re-planned position of the remaining ports.

9. The robotically-assisted surgery method according to claim 8, further comprising:
deriving a priority of piercing the remaining ports on the body surface; and
causing the display unit to display information of piercing order regarding the priority.

10. The robotically-assisted surgery method according to claim 8, further comprising:
designating an inappropriate port which is included in the plurality of ports and which is inappropriate to be pierced, wherein a distance between the inappropriate port and a port which is not designated as the inappropriate port among the plurality of ports is equal to or longer than a threshold.

11. The robotically-assisted surgery method according to claim 8, further comprising:
causing the display unit to visualize the 3D data with an annotation of the information of the remaining ports.

12. The robotically-assisted surgery method according to claim 8, further comprising:
causing a projection unit to project visible light representing information of the remaining ports to the body surface.

13. The robotically-assisted surgery method according to claim 8, further comprising:
performing a pneumoperitoneum simulation on volume data of the subject to generate the 3D data of a virtual pneumoperitoneum state.

14. The robotically-assisted surgery method according to claim 8, further comprising:
causing the display unit to visualize the 3D data with an annotation of the information of the position of at least one of the remaining ports and the position planning information of the at least one of the remaining ports.

15. A robotically-assisted surgery system of a robotically-assisted surgical device configured to assist robotic surgery with a surgical robot that includes a first robot arm holding a first surgical instrument, a second robot arm holding a second surgical instrument, and a third robot arm holding a third surgical instrument, at least one of the first surgical instrument, the second surgical instrument, and the third surgical instrument being an endoscope, the robotically-assisted surgery system comprising a processing unit configured to:
acquire 3D data of a subject;
acquire kinematic information regard to the first robot arm, the second robot arm, and the third robot arm of the surgical robot for performing the robotic surgery;
acquire information of a surgical procedure for operating the subject;
acquire position planning information for a plurality of ports which are to be pierced on a body surface of the subject and include a first port and remaining ports other than the first port, the position planning information including planned positions of the first port and the remaining ports, the first surgical instrument being inserted into the first port and the second surgical instrument and the third surgical instrument being respectively inserted into the remaining ports;
when the first port is pierced on the body surface and the remaining ports are not pierced on the body surface, acquire measurement information obtained by measuring a position of the first port which is pierced on the body surface;
determine a re-planned position of at least one of the remaining ports that are not pierced on the body surface, based on the position planning information including the planned position of the first port on the body surface, the measurement information of the position of the first port which is pierced on the body surface, the information of the surgical procedure, the kinematic information, and the 3D data; and
cause a display unit to display information indicating the determined re-planned position of the remaining ports.

16. The robotically-assisted surgery system according to claim 15, wherein the processing unit is further configured to:
derive a priority of piercing the remaining ports on the body surface; and
cause the display unit to display information of piercing order regarding the priority.

17. The robotically-assisted surgery system according to claim 15, wherein the processing unit is further configured to:
designate an inappropriate port which is included in the plurality of ports and which is inappropriate to be pierced, wherein a distance between the inappropriate port and a port which is not designated as the inappropriate port among the plurality of ports is equal to or longer than a threshold.

18. The robotically-assisted surgery system according to claim 15, wherein the processing unit is further configured to:
cause the display unit to visualize the 3D data with an annotation of the information of the remaining ports.

19. The robotically-assisted surgery system according to claim 15, wherein the processing unit is further configured to:
cause a projection unit to project visible light representing information of the remaining ports to the body surface.

20. The robotically-assisted surgical system according to claim 15, wherein the processing unit is further configured to:
cause the display unit to visualize the 3D data with an annotation of the information of the position of at least one of the remaining ports and the position planning information of the at least one of the remaining ports.

* * * * *